United States Patent
Karvela et al.

(10) Patent No.: US 10,283,219 B2
(45) Date of Patent: May 7, 2019

(54) WEARABLE DEVICE

(71) Applicant: DNANUDGE LIMITED, London (GB)

(72) Inventors: Maria Karvela, Cambridge (GB);
Christofer Toumazou, London (GB)

(73) Assignee: DNANUDGE LIMITED, London (GB)

(*) Notice: Subject to any disclaimer, the term of this patent is extended or adjusted under 35 U.S.C. 154(b) by 0 days.

(21) Appl. No.: 15/649,804

(22) Filed: Jul. 14, 2017

(65) Prior Publication Data
US 2017/0323057 A1 Nov. 9, 2017

Related U.S. Application Data

(63) Continuation-in-part of application No. PCT/GB2016/053052, filed on Sep. 30, 2016, which
(Continued)

(30) Foreign Application Priority Data

Oct. 1, 2015 (GB) .................................. 1517393.3
Feb. 26, 2016 (CN) ..................... 2016 2 0146860 U
Aug. 1, 2016 (GB) .................................. 1613229.2

(51) Int. Cl.
*G16H 10/40* (2018.01)
*G16H 10/65* (2018.01)
(Continued)

(52) U.S. Cl.
CPC .......... *G16H 10/65* (2018.01); *A44C 5/0015* (2013.01); *G06F 1/163* (2013.01);
(Continued)

(58) Field of Classification Search
None
See application file for complete search history.

(56) References Cited

U.S. PATENT DOCUMENTS 5,478,989 A 12/1995 Shepley
6,025,281 A 2/2000 Passlack et al.
(Continued)

FOREIGN PATENT DOCUMENTS

EP   1 329 835 A1   7/2003
WO   03/027236 A2   4/2003
(Continued)

OTHER PUBLICATIONS

International Search Report, dated Mar. 6, 2017, and Written Opinion issued in corresponding PCT Application No. PCT/GB2016/053052.

*Primary Examiner* — David L Lewis
*Assistant Examiner* — Shauna-Kay Hall
(74) *Attorney, Agent, or Firm* — Saul Ewing Arnstein & Lehr LLP

(57) ABSTRACT

A wearable device comprising a memory storing a database of product codes and associated product recommendations derived from personalised biological information, a product code reader for reading a product code or data from a product, and a processor for using a read product code or read data to perform a look-up in the database to obtain a product recommendation for the associated product. The wearable device further comprises an indicator for providing an indication of the obtained product recommendation to a wearer of the device.

12 Claims, 17 Drawing Sheets

Specification includes a Sequence Listing.

Related U.S. Application Data is a continuation of application No. 15/152,921, filed on May 12, 2016.

(51) Int. Cl.

| | | |
|---|---|---|
| *G16H 40/63* | (2018.01) | |
| *G06F 1/16* | (2006.01) | |
| *G06F 17/30* | (2006.01) | |
| *G06K 7/10* | (2006.01) | |
| *A44C 5/00* | (2006.01) | |
| *G06Q 30/06* | (2012.01) | |
| *G06F 19/00* | (2018.01) | |
| *G06Q 10/10* | (2012.01) | |

(52) U.S. Cl.
CPC ........ *G06F 17/30241* (2013.01); *G06F 19/00* (2013.01); *G06K 7/10861* (2013.01); *G06Q 30/0631* (2013.01); *G16H 10/40* (2018.01); *G16H 40/63* (2018.01); *G06Q 10/10* (2013.01)

(56) References Cited

U.S. PATENT DOCUMENTS

| | | | |
|---|---|---|---|
| 6,652,455 B1 * | 11/2003 | Kocher | G06F 19/326 600/300 |
| 7,805,319 B2 | 9/2010 | Badinelli | |
| 9,414,623 B2 * | 8/2016 | Minvielle | A23P 10/00 |
| 2003/0134679 A1 * | 7/2003 | Siegel | A63F 13/005 463/43 |
| 2004/0103033 A1 * | 5/2004 | Reade | G06Q 20/20 705/16 |
| 2004/0143447 A1 | 7/2004 | Lay | |
| 2008/0263011 A1 | 10/2008 | Badinelli | |
| 2010/0113892 A1 * | 5/2010 | Kaput | G06F 19/00 600/301 |
| 2010/0169340 A1 * | 7/2010 | Kenedy | G06Q 30/02 707/758 |
| 2010/0312668 A1 | 12/2010 | Notsani | |
| 2011/0166881 A1 | 7/2011 | Brazzo et al. | |
| 2011/0318717 A1 * | 12/2011 | Adamowicz | G09B 19/0092 434/127 |
| 2013/0023058 A1 * | 1/2013 | Toumazou | G06F 19/3475 436/501 |
| 2013/0337974 A1 | 12/2013 | Yanev et al. | |
| 2014/0090039 A1 * | 3/2014 | Bhow | H04W 12/06 726/7 |
| 2014/0107932 A1 | 4/2014 | Luna | |
| 2014/0214623 A1 * | 7/2014 | Cancro | G06Q 30/0241 705/26.63 |
| 2015/0073907 A1 * | 3/2015 | Purves | G06Q 20/32 705/14.58 |
| 2015/0170249 A1 * | 6/2015 | Cockcroft | G06Q 30/0627 705/26.63 |
| 2015/0242837 A1 * | 8/2015 | Yarbrough | G06Q 20/327 705/44 |
| 2015/0317503 A1 * | 11/2015 | Powell | G06K 7/10831 235/455 |

FOREIGN PATENT DOCUMENTS

| | | |
|---|---|---|
| WO | 2005/027716 A2 | 3/2005 |
| WO | 2008/019695 A2 | 2/2008 |

\* cited by examiner

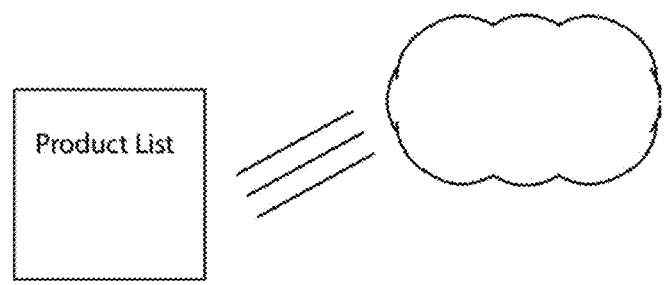
Figure 13
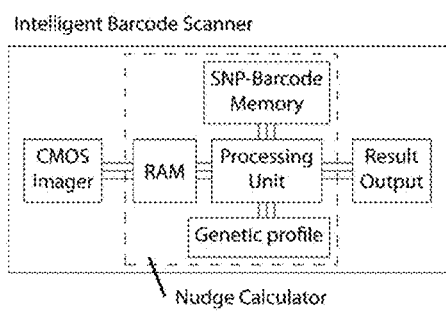
Figure 14
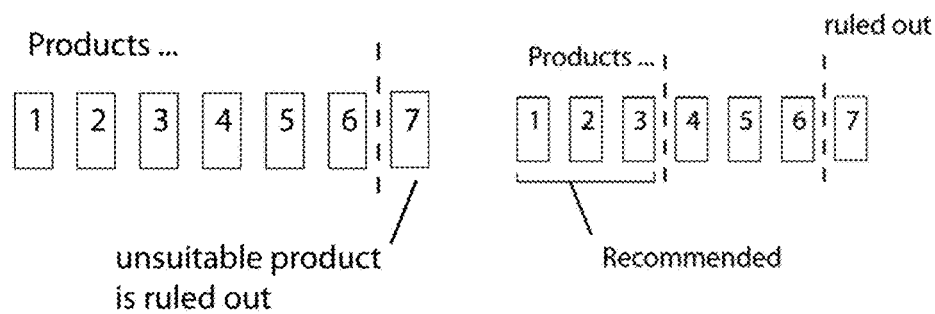
Figure 15
Figure 16

WEARABLE DEVICE

CROSS-REFERENCE TO RELATED APPLICATIONS

This application is a continuation-in-part of International Application No. PCT/GB2016/053052, filed Sep. 30, 2016, which claims priority to GB Application No. GB1517393.3, filed Oct. 1, 2015; Chinese Application No. CN201620146860.0, filed Feb. 26, 2016; U.S. application Ser. No. 15/152,921, filed May 12, 2016; and GB Application No. GB1613229.2, filed Aug. 1, 2016, the entire contents of each of which being fully incorporated herein by reference.

FIELD OF THE INVENTION

The present invention relates to a method, apparatus and system for securely transferring to consumers' biological information, such as genetic and/or microbiome information, and/or further information related to biological information, between computer systems and devices. Such information may be used for the purpose of purchasing a product or service of choice. The present invention also relates to a method and apparatus for providing product recommendations. An example of such an apparatus may be a wearable device for providing product recommendations.

BACKGROUND OF THE INVENTION

Advancements in sequencing and healthcare technologies and breakthroughs in science have revolutionised the field of genetics and microbiome data analysis and interpretation, making such services cost-effective and accessible to the general public. Every day new genetic traits are being described, generating a continuously expanding catalogue of biomarkers that affect the health, wellbeing, and, in the case of genetic variations phenotype, of living organisms, including humans, animals, microbes, fungi, and plants.

Identifying individual differences at a molecular and cellular level has allowed for a deeper layer of personalisation in medicine, such as for drug dosage and treatment selection, as well as in lifestyle improvement and management, by tailoring personal care products ranging from cosmetics and nutraceuticals, to services that enhance fitness, weight-loss regimes etc. A number of private companies and clinics have been created in order to cater for the growing consumer genetics or healthcare markets. Nevertheless, limitations in the technologies utilised restrict the commercialisation of such approaches to lab-based services, compromising delivery speed, business models and privacy. Depending on the samples they work on, this may require the user/customer/patient to compromise on privacy and convenience.

Currently, an individual that wants to gain access to information related to his/her genetics or health condition, whether for a specific purpose/concern or for general interest, needs to go through a private clinic or professional body, provide sample to central labs (either in person or by post). Such a process is time consuming, inconvenient and may invade the individual's privacy. For example, many tests are based on blood analysis, which requires the individual to attend a sample collection session with an expert. In the most convenient available approach, he/she needs to order a kit for collecting saliva sample and then post it to the lab. The individual must avoid eating and drinking for certain time, and is responsible for handling the sample collection process.

A conventional process for personalised medical testing is as follows:
1) Order online a sample collection kit from the service provider;
2) Receive the kit and collect the biological sample (usually saliva)—at this stage, the customer may also be asked to fill in a questionnaire that will be analysed together with the test results;
3) Send the sample back to the service provider via post; the sample will then be processed by skilled lab staff, e.g. using various genetic analysis assays; and
4) 4-8 weeks later, the customer will be sent electronically or via post a generic analysis report, e.g. listing his/her different variations in the DNA. In some cases, the service provider may make a product recommendation or offer a bespoke product designed or selected according to the client's test results.

These conventional approaches require the costumer to send his/her biological sample to some remote location, usually via post, in order to be processed and analysed. This introduces confidentiality concerns with regards to:
1) who analyses the biological sample and how and where this is done;
2) how and where the genetic or health information is stored, or safely discarded;
3) how is the customer's personal information linked to his/her genetic or health profile;
5) who can have access to the customer's health information (especially when the information is as personal as genetic information);
6) in many cases, prior to releasing the analysis report, the customer is asked to fill in questionnaires in relation to his/her medical history, lifestyle habits etc—sharing such information adds another level of concern.

At this point it should be highlighted that confidentiality concerns are not solely related to the genetic results, i.e. what genetic variants the customer carries, but also relate to the personal concerns that motivated the customer to consider having a genetic test, for instance predisposition to impotence, baldness, drug addiction, alcoholism etc. If this information were to become available to health insurance providers, potential employers etc, an individual could be "genetically stigmatised" and "classified". The impact on an individual life could be enormous.

The majority of the currently available genetic services offer wide genome screening; e.g., using a predefined platform tagged with more than 100,000 biomarkers and screening irrespectively all client samples for all genetic biomarkers. This means that a high proportion of customers are being screened by default for genetic traits that they may not want to know about; for instance, an individual purchasing a test in order to determine his/her predisposition to detoxification will be also screened for serious neurodegenerative diseases such as Alzheimer's and Parkinson's disease. Access to information related to concerns that the customer did not initially have, may have a detrimental effect on the individual's socio/psychological balance.

On the other hand, the majority of such services and tests focus on the individuals themselves, whereas the reality is that we are not the only living thing influencing our lives. We are living with hundreds of thousands of bacteria in our body, good and bad. In order to provide an effective personalized solution, we need to take these bacteria into account. Companies like uBiome (http://ubiome.com/) have started providing direct-to-consumer services to analyse the gut microbiome. But similarly, they require the customer to undergo a process as:
1—Order a kit online;
2—Collect own fecal matter;
3—Post the sample back to lab;
4—Wait for several weeks.

Besides the long turnaround time, some people might avoid this process because they are uncomfortable providing the type of sample required. Therefore, this process is not a fully compliant model.

A further disadvantage of many of the services available today is that much of the information provided remains greatly un-interpretable and, consequently, of no interest or relevance to his/her day-to-day life. Whilst some services do offer to the customer personalised services or products, these may compromise the customer's freedom of choice and selection, and they do not take into account an individual's personality and idiosyncrasy, including lifestyle choices, as well as religious, political, and cultural beliefs. For instance, a diet plan high in red meat intake may be recommended for a person who is genetically prone to not absorbing iron, even if the person is vegetarian or simply dislikes red meat. Another example might be a service that provides a tailored personal care product, based on a customer's genetic traits, which has been tested on animals. Such a product, even if specifically designed to the individual's genetic profile, may conflict with his/her views on animal welfare.

Finally, it will be appreciated that in a fast moving world where time is a very important choice-making criterion, the speed with which results are provided is key. The fact that, currently, a biological sample has to be sent off remotely to a laboratory to be processed, means the costumer can be waiting weeks or even months for the results. The longer the time gap between ordering a genetic test and receiving the results/recommended product, the more likely it will be that the customer fails to follow-up with associated purchases.

Taking into consideration the above, it becomes apparent that services that require the sending of biological samples to be processed remotely are often not very attractive from a consumer and/or a business point-of-view. Furthermore, currently results are generally problem-based rather than solution-based. This highlights the desire for services offering testing that a) can be performed by the consumer in his/her own private environment, b) are based on targeted personal (e.g. genetics and microbiome) traits due to the customer's specific concerns, c) provide immediate, actionable results, and d) are delivered quickly, reliably, and securely.

Breath comprises about 3,000 compounds. Recent discoveries have indicated the potential of breath analysis for understanding cellular activities in the body. It is a non-invasive and highly compliant test to do.

The compounds in the breath are from the exhaust and waste of the cellular activates. They shed into blood and get exhaled from the lungs. Each blood circulation takes about 1 minute. Therefore, analysing breath can indirectly help in analysing the whole body, either during that minute, or over a longer period if the samples are accumulated. This has made breath analysis an attractive method to evaluate body condition. It has been used for many medical and non-medical applications, such as:
Alcohol level in blood
Early detection of cancer
Infectious disease
Asthma stratification
Bowel preparation
Irritable bowel syndrome
Lactose maldigestion and intolerance
Analysis of microbiome, e.g. *Helicobacter pylori*
Chylomicron remnant metabolism
Etc For each of these tests, certain bio-markers are analysed. For example, different levels of certain volatile organic compounds may indicate early stages of developing different cancers like lung, colorectal, breast, prostate, etc. They are increased because of the different function of the tumour cells. Or the test might be on $CH_4$ and $H_2$ to analyse lactose mal-digestion and intolerance.

There have been different technologies developed to enable such tests, from mass spectrometry in labs to hand-held breathalysers for alcohol tests, with different complexities and accuracies. For example, Field Asymmetric Ion Mobility Spectrometry (FAIMS) developed by Owlstone Medical is a miniaturised semiconductor sensor that allows high-precision separation and measurement of breath compounds. Owlstone Medical has portable devices on breath analysis and breath sample collection. Such a platform potentially may allow integration of the sensors in mobile devices.

SUMMARY OF THE INVENTION

Whilst it is known that analysis of a biological sample can be used to determine, for example, the benefits and risks associated with products and activities, there are currently no commercial services that integrate home testing with product and service recommendations whilst at the same time ensuring security of biological information. What is proposed here is a service that integrates the home test, via the Internet, with a back-end results analysis service resulting in the provision to users of product and service recommendations. The service does not disclose biological information, such as genetic or microbiome information, outside of the back-end provider, rather making use of biological filter codes. Such filter codes can be used for secure product mapping without disclosing genetic information or microbiome information.

According to a first aspect of the present invention there is provided a method of providing a user with analysis of test results for a biological sample. A test kit suitable for performing a test on said biological sample is selected or provided, the test kit comprising one or more biomarkers for one or more areas of interest to the user. The test kit is provided to the user. The biological sample is then applied to the test kit in order to generate test results dependent upon said biological marker(s), and the test kit coupled to a computer device of the user, either before, during or after applying the biological sample to the test kit, and sending the test results from the computer device, via the Internet or another suitable network, to said remote, secure server site. At the secure server site, the test results are processed to generate an analysis of the data and the analysis sent from the server site to the user's computer device, or to another device, via the Internet or the other suitable network.

The biological sample may be derived from the microbiome of the user.

The test kit may consist of a unit that the person can breathe into. The unit is connected to a sensing device that allows identifying and measuring the level of volatile organic compounds. The results from the measurement may be patterns of signals. An example of such unit may be the breathing mask and gas sensor developed by Owlstone Medical. The breathing mask (ReCIVA) allows collection of the breath sample and the FAIMS sensor allows measuring the level of the compounds in the breath.

The computer device may be any suitable device, such as a laptop, pc, or smartphone. The computer device may be a wearable device.

The area of interest may be one of a lifestyle area, a product or service or plural products or services, product ingredients, or a category of products or services.

The method may comprise obtaining the biological sample from a sample extracted locally from or by the user, or from a container storing a sample extracted remotely. The test kit may comprise a test module having a multiplicity of addressable test sites each of which is capable of independently carrying out a test for a biomarker that may be located at the test site, the or each said identified biomarker being provided at a test site. The method further comprises sending, together with said test results, an address of the test site(s) at which the identified biomarker(s) is(are) provided, the method comprising, at the secure server site, identifying a biomarker using the associated test site address. The method is such that the biomarker is not identifiable from the sent data alone.

The analysis may comprises one or more biological filter codes/patterns. These codes/patterns may, for example, define characteristics of an individual that result from the individual's genetic or microbiome makeup, but without identifying that genetic or microbiome makeup itself.

The method may comprise installing a browser plug-in to a web browser on said computer device, the browser plug-in causing the browser to facilitate filtering of product and/or service information displayed in a browser window on the basis of said analysis.

The method may comprise making all or a part of the analysis available to an application installed on the computer device to facilitate filtering of product and/or service information, or the provision of advice, by the application. The application may be configured to obtain product and/or service information read from a product or service label by the computer device.

The analysis may comprise an identification of a product or service or a range of products or services. The analysis may also comprise web links facilitating online purchase of the products or services.

The step of identifying one or more biomarkers relevant to the or each area of interest comprises performing a lookup in a database of or coupled to said remote secure server site, mapping areas of interest to biomarkers.

The data identifying the biomarker(s) may not be provided to, or stored at, the user device or other device.

The method may comprise providing to the user device or other device a user public-private key pair, whilst providing to the remote secure server site the user public key, the method comprising encrypting said (coded) analysis at the remote secure server site with the user public key and decrypting it upon receipt at the user device or other device using the user private key.

The or each biomarker may be a primer suitable for use in DNA synthesis.

The or each biomarker may be a volatile organic compound level in the breath.

The test kit may comprise a breathing unit and a gas sensor unit with necessary circuitry and processing modules.

The test kit may comprise an array of Ion Sensitive Field Effect Transistors, optical sensors, nanopores, nanowires and any other form of microarray.

The method may also comprise receiving from the user computer, via a web portal, an identification of one or more areas of interest to the user and, at the remote secure server site, identifying one or more biomarkers relevant to the or each area of interest.

According to a second aspect of the present invention there is provided a method of providing product advice to an individual, the method comprising reading data on product label using a computer device, interpreting the data using coded biological data stored on the device, the biological data relating to the individual and having been previously obtained by means of an analysis of a biological sample (e.g. breath) obtained from the client, and based on the interpretation, presenting on a display of the device advice relating to the product, the advice being tailored to the individual. Said advice may relate to the suitability of the product to the individual, and may recommend a further analysis of a biological sample, that further analysis being relevant to the product.

Said data may be contained within a computer readable code of the product label, such as a QR code or a barcode.

According to a third aspect of the present invention there is provided a wearable device comprising a memory storing a database of product codes and associated product recommendations derived from personalised biological (e.g. genetic or microbiome) information, a product code reader for reading a product code from a product, and a processor for using a read product code to perform a look-up in the database to obtain a product recommendation for the associated product. The device further comprises an indicator for providing an indication of the obtained product recommendation to a wearer of the device.

The device may be configured as a wristband or as a module attachable to a wristband, although it may take other forms such as a key fob, ring, or necklace.

A wearable device according to this aspect of the invention addresses a number of shortcomings with the prior art approaches. In particular it can restrict the type and amount of personal genetic information that is held or sent outside of the wearable device. This reduces or eliminates the risk of a user's genetic information leaking out to third parties. It also makes the service useable in environments where (wireless) network connections are unavailable or insecure. Furthermore, by providing a service by means of a wearable device, it becomes possible to integrate into the service measurements and data collected direction from the wearer. For example, it becomes possible to modify the locally held data, or adapt a result, in dependence up local collected physiological and/or biochemical and/or activity data. For example, one can envisage a service which is able to provide a product recommendation based upon a user's personal genetics, but modify that recommendation based upon sensed data that the user has recently engaged in exercise.

The product code may be a barcode in which case the product code reader is a barcode reader. The barcode reader may comprise a photo-imaging device such as a camera. The barcode reader may use optical components shared with a physiological sensor of the device. The device may further comprise an optical projector for projecting a targeting light onto a product to aid alignment of the photo-imaging device with a barcode.

By way of example, the indicator may comprise one or more of a display screen, coloured lights, a vibration motor, and a sound generator.

The device may comprise one or more physiological and/or biometric sensors and/or biosensors for monitoring a wearer, and a processor for dynamically updating product recommendations in the database using sensed data.

The processor may be configured to receive a user input to switch on or off dynamic updating of the product recommendations.

The device may comprise a wireless transceiver for communicating with a peer wearable device to exchange information within respective databases, and a processor for recalculating the product recommendations using a combination of the received data and the existing data. The device may further comprise a proximity detector for initiating an exchange of data with a peer device when the devices are in close proximity to one another.

The database may comprise product codes and associated product recommendations derived from personalised microbiome information for each of a plurality of individuals, further comprising an interface for receiving a user selection of one of the individuals.

The database may include markers to identify products whose recommendation is influenced by hereditary personalised biological (e.g. genetic or microbiome) information, the device comprising means for receiving a user input to filter products based on said markers.

The device may comprise a user interface for receiving from a user a notification of a product purchase, and means for storing that indication in the database. The user interface may be configured to receive from a user a notification that a product should be removed from the database.

The device may comprise a processor for automatically identifying the wearer, e.g. using voice recognition, biometric data, physiological data etc.

The personalised biological information may comprise personalised genetic and epigenetic information.

The device may be configured to operate in a low power sleep mode and a relatively high power active mode, the device being operable in the sleep mode to recognise a generic product code and cause a switch to the active mode.

The device may comprise a geographic location system for detecting the location of the device, a processor being configured to make accessible or inaccessible related parts of the database in dependence upon the detected location.

According to a fourth aspect of the present invention there is provided a system comprising a wearable device according to the above third aspect of the present invention and a computer device for communicating wirelessly with the wearable device in order to populate and/or update said database. The computer device may be a smartphone.

The computer device may comprise a memory storing said personalised genetic information and may be provided with an application for managing the wearable device. Data to populate or update the database may be retrieved by the computer device from a cloud network.

According to a fifth aspect of the present invention there is provided a method of conducting an online purchase of a product or service. The method comprises, at a user computer device, storing one or more biological (e.g. genetic) filter codes, the biological filter codes mapping to respective products or services or categories of products or services but not explicitly identifying a user's genetic or biological information. A web browser or application installed on the user computer device is used to retrieve available product or service data from a web portal. The filter code(s) are used to identify available products or services that are suited to the user's genotype or microbiome. The suited products or services are identified to the user via a display or other user interface of the user's computer device.

According to a sixth aspect of the present invention there is provided a system for providing a user with analysis of test results for a biological sample, comprising:

a) a computing device;
b) a communication network to which the computing device is connected;
c) a secure server remote to and connected with the computing device via the communication network;
d) a test kit connected to the computing device; the test kit further comprising one or more biomarkers identified by the secure server based on an identification of one or more areas of interest to a user from the computing device;

wherein, the test kit is capable of receiving a biological sample and generating test results based thereon; the secure server capable of generating an analysis based on the test results transmitted from the computing device to the secure server via the communication network.

According to a further aspect of the present invention there is provided a wearable device comprising a memory storing a database of product codes and associated product recommendations derived from personalised biological information, a product code reader for reading a product code or data from a product, and a processor for using a read product code or read data to perform a look-up in the database to obtain a product recommendation for the associated product. The wearable device further comprises an indicator for providing an indication of the obtained product recommendation to a wearer of the device.

BRIEF DESCRIPTION OF THE DRAWINGS

FIG. 3 illustrates schematically a web browser window including a new service button provided by a browser plug-in;

FIG. 13 illustrates the use of the cloud to inform product recommendations;

FIG. 14 illustrates schematically components of a wearable device;

FIGS. 15 and 16 illustrate a product recommendation scheme;

DETAILED DESCRIPTION

Semiconductor nanotechnology and optical technologies have made significant contributions to people's lifestyle, especially by facilitating hardware miniaturisation. Its application to the sequencing and genotyping industry has enabled so-called "lab-on-chip" systems. Depending on the biological questions/genes of interest, primer(s)/probe(s)—more generally referred to as "biomarkers"—are designed accordingly. A biomarker is an oligonucleotide such as a DNA molecule and may target certain gene(s)/variation(s). A biomarker may alternatively, for example, be an antibody or an antigen. By applying/choosing different types of biomarkers on such systems, a customer can test his/her biological sample, DNA, RNA, protein etc, (extracted locally or remotely by a third party from e.g. saliva, blood, urine, tissue, stool, hair etc) for specific traits, as dictated by certain lifestyle concerns or interest.

A service and technology will now be described which will open a new era in consumer genetic services; it offers speedy, direct-to-consumer, targeted genetic testing with actionable results, while at the same time ensuring maximum levels of privacy and confidentiality. The customer can have complete control over the type of the genetic test (i.e. biomarkers), his/her biological sample, ownership and full access to the genetic results, and, ultimately, freedom to choose from a genetically-suitable range of products and services that that best matches his/her own personality, preferences, and lifestyle. Whilst the following examples relate to analysing the genotype of a human individual, there is no reason why the service cannot be extended to encompass other living organisms including animals, plants, microbes, fungus, etc.

Figure 1:
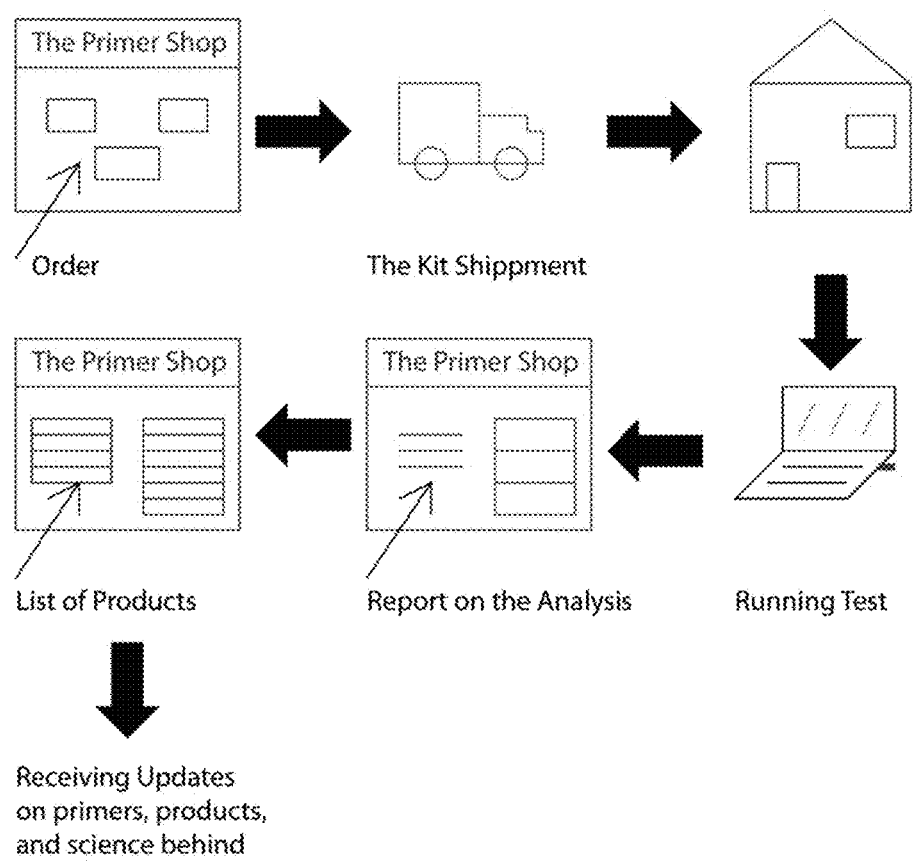
FIG. 1 illustrates schematically a service for allowing a customer to perform a test on genetic material or microbiome, and for providing the customer with an analysis of the results and product/service recommendations.

FIG. 1 presents an overview of the service which is first accessed by a customer via a web portal, referred to here as "THE PRIMER SHOP™". Although not discussed here in any detail, THE PRIMER SHOP operates a number of servers connected to the Internet and which host the service offered by THE PRIMER SHOP. Via the web portal, THE PRIMER SHOP offers a catalogue of biomarkers, more specifically primers, with each primer/set of primers being associated with a lifestyle concern/question, e.g.;

"how does my body metabolise caffeine?",

"what is the best vitamin supplement for me?",

"what is the best treatment to help me quit smoking?",

"how fast does my body recover from injury?" etc.

Although not exclusively the case, exemplary primers may be a strand of short nucleic acid sequences that serves as a starting point for DNA synthesis. As is known in the prior art, such primers can be used in the detection of genetic single-nucleotide polymorphisms (SNPs) and more particularly to determine the variation type (or allele) of a tested individual for a given SNP. The primer(s) or multiplex array of primers could be immobilised on the cartridge.

The available primers may be clustered based on the specific field of application, e.g. weight-loss, fitness, nutrition etc. For example, a customer looking for a personalised workout can choose from a list of primers used to analyse genes affecting fitness and diet. The number of primers suggested by THE PRIMER SHOP depends on the complexity of the question. However, the actual number of primers selected for the test is customer-dependant; in general, the more primers used in the assay, the more refined the analysis will be. THE PRIMER SHOP may offer primer bundles to the customer, especially where the chosen primers are shared within different applications (e.g. primer A can be used to advise regarding fitness and nutrition). Each primer configuration may be purchased online or within a retail store.

Alternatively, a customer may seek to use THE PRIMER SHOP services due to concerns/questions about a specific product (or category of products), and the impact the product (or category of products) may have on the individual based on his/her genetic background. In this case, THE PRIMER SHOP may suggest to the individual a customisable platform with one or more biomarkers, in order to evaluate the suitability or the effect of the specific product/category of products based on the test results. For instance, a customer may be concerned about the consumption of a particular brand of chocolate bar, presenting THE PRIMER SHOP with the question "how good or bad is for me is the daily consumption of a "BRANDX" chocolate bar?". Based on the ingredients and nutritional content of this product (outlined at Table 1 below), THE PRIMER SHOP may recommend to the customer a testing platform with a selection of genetic biomarkers evaluating, e.g. diet response, genetic variants related to the metabolism of sugar, sodium, cholesterol, carbohydrates, saturated fats and genetic risk for elevated LDL, ability to convert beta-carotene to vitamin A, predisposition to lactose intolerance etc. Based on the results, THE PRIMER SHOP will be able to assess the suitability of this product/category of similar products for the consumer, as dictated by the consumer's genetic code.

One suitable technology for testing a customer's genotype is that provided by DNA Electronics, London, UK. This technology utilises arrays of chambers/aliquots, each with particular primers immobilised therein. Different primers target different variations of different genes. Ion Sensitive Field Effect Transistors (ISFETS) are located within the chambers to sense reactions, e.g. pH changes, resulting from the addition of bases to the extending primers. Alternatively, other sensing platforms can be used, such as optical, nanowire and nanopore. Other suitable technologies based on DNA analysis include, for instance, those provided by Epistem Ltd, QuantumDx Group Ltd, and Cepheid UK Ltd, as well as non-DNA based platforms, such as those provided by Cambridge Nutritional Services Ltd, or Imutest Ltd, which utilise antigen-antibody interactions.

Figure 6:
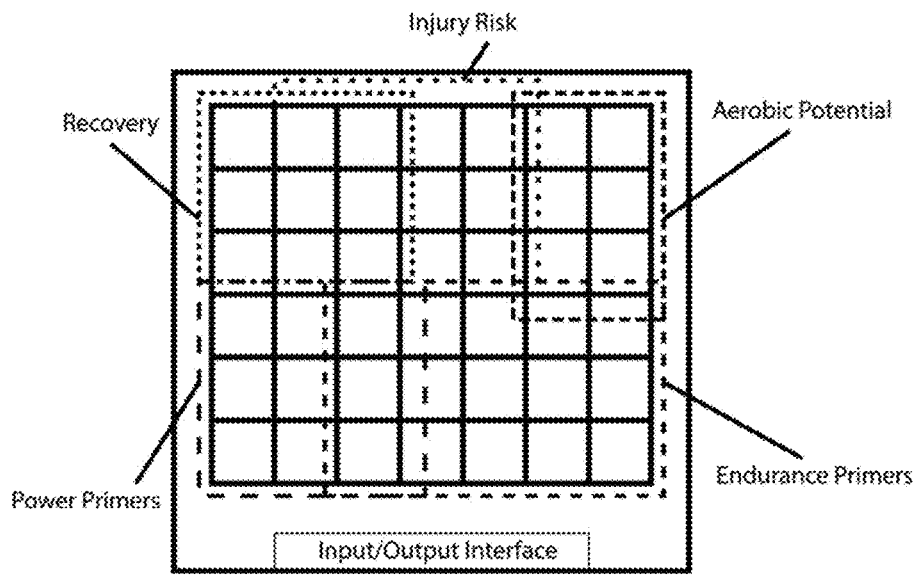
FIG. 6 illustrates schematically a DNA test module including an array of tests sites.

THE PRIMER SHOP may have different pre-prepared arrays that cover a variety of applications. For example, a DNA test module 1 may have primers both for various aspects of fitness—as illustrated in FIG. 6—and nutrition. Depending on the customer's interest, only the part that is asked for may be accessible to the customer (either by physically preventing the running of a test at non-accessible parts, or by preventing access to the results). This selection is based on the customer's expressed interest and/or purchase and is implemented remotely via THE PRIMER SHOP portal.

A "plug-and-play" test module of a DNA test kit can be purchased either preloaded with the primers, or customised according to the customer's specific questions/concerns, e.g. with specific primers printed into chambers of the test module. The identity of particular primers and their locations loaded onto the module are not disclosed to the customer and are known only to THE PRIMER SHOP. THE PRIMER SHOP maintains a database of available/supplied modules mapping module reference ID to primers and their locations (this data is not associated with customer identities). After deciding on the set of primers which is relevant to the lifestyle concern/question or product/category of products of interest to the customer, the customer may proceed with the order. The customer pays only for the tests/primers that he/she is interested in. Privacy is secured with regards to a) the selected primers, and b) the genetic results. THE PRIMER SHOP does not disclose the genetic sequence of the primers, nor their exact location on the testing platform, to the customers or to any third parties. Moreover, the point-of-care nature of the kit eliminates the time lag and gives information that the customer wants at the point that he/she wants it.

Figure 2:
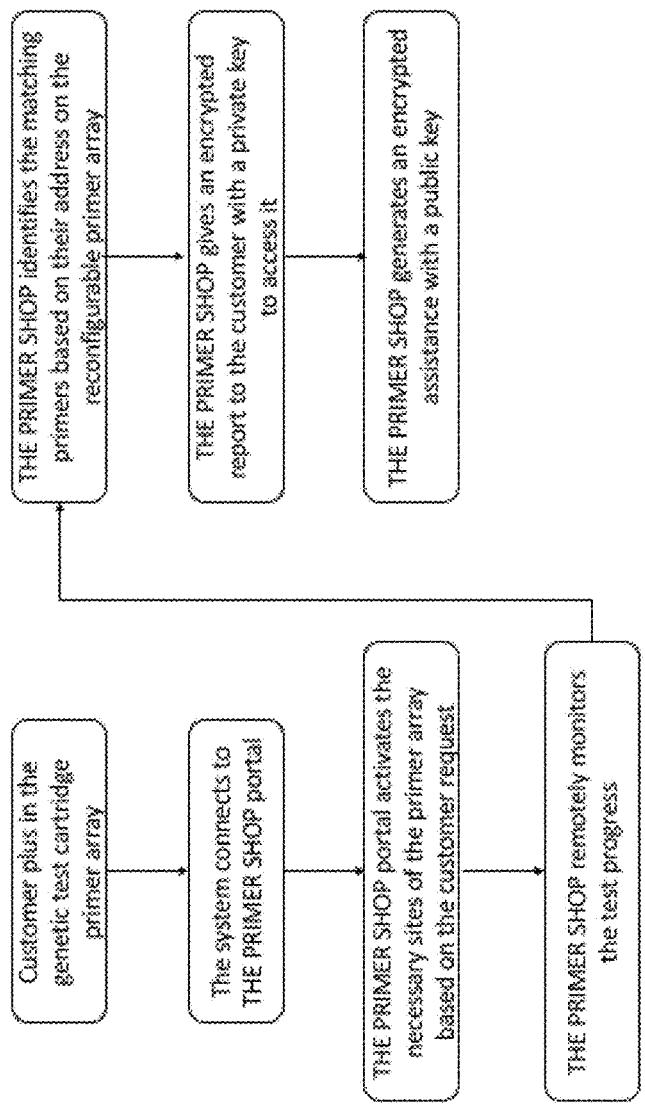
FIG. 2 is a flow diagram further illustrating the service of FIG. 1.

THE PRIMER SHOP's testing kit, including the plug-and-play DNA test module will be delivered to the customer's address. A sample preparation kit can be also sent to the customer in order to perform locally the sample extraction; otherwise, sample extraction could be performed remotely by a third party. The procedure of FIG. 2 is then followed. The customer can run the test by following the instructions, including loading the biological sample on the testing platform, plugging the test module into his home computer (or mobile device, e.g. a smartphone), e.g. using the computer device's USB port. Via an Internet connection, the customer's computer device connects to THE PRIMER SHOP (TPS) portal. THE PRIMER SHOP remotely initiates the test. In the case where the DNA test module includes a number of sites, with or without primers present, this involves THE PRIMER SHOP activating those sites where primers are present and which are required (e.g. paid for) by the customer. As the test is run, THE PRIMER SHOP remotely monitors progress.

In an exemplary procedure, the module delivers to a server (at THE PRIMER SHOP) data generated by active test sites on the device. Data is accompanied by a module reference ID read from the module and the location(s) (e.g. array address(es)) from which it originates. As only THE PRIMER SHOP knows the primer that is located at a given location for a given module (identified by the reference ID), no confidential genetic information is made available at the customer's computer device or to any intermediate location in the Internet. This provides a level of security that exceeds even that which can be achieved by encryption (although the transferred data may additionally be encrypted).

The test result data is received by THE PRIMER SHOP server and decrypted if necessary (the test module may include a memory storing a public key of a public/private key pair of THE PRIMER SHOP, allowing the customer's computer device to encrypt data it sends to THE PRIMER SHOP). It is then analysed, using THE PRIMER SHOP's knowledge of the primers that have been used on the test module identified by the module reference ID and a database of characteristics that have been mapped to potential results. For example, certain alleles may be mapped to certain characteristics.

Based on the test outcome and analysis, THE PRIMER SHOP generates a summary report of the results. This might be a written report that summarizes the results and provides an accompanying discussion including certain general advice and recommendations. THE PRIMER SHOP additionally generates or applies one or more genetic filter codes based on the test results. These codes are mapped to certain product and/or service properties. For example, a code "A123" may map to the property "gluten free". The codes are encrypted with the private key of THE PRIMER SHOP or with a symmetric key known only to THE PRIMER SHOP.

THE PRIMER SHOP sends the summary report of the results (answering the customer's initial question) to the client's device (or using some messaging service such as email, text etc), together with the generated or identified encrypted code(s), without disclosing the actual genotype of the individual. The report and accompanying encrypted code(s) are preferably encrypted, for example using the public key of the public/private key pair provided to the customer on the DNA test module—the customer may send its public key to THE PRIMER SHOP together with the test result data (THE PRIMER SHOP does not keep a copy of the user's private key).

THE PRIMER SHOP may additionally identify to the customer a range of products or services suited to the customer's genotype with an option to purchase. The customer can select from these products and/or services depending on his/her personal preferences, e.g. price, eco-friendliness of product packaging, brand preference, etc. The Primer Shop may subsequently keep the customer updated about new tests, products and scientific discoveries. These updates will be sent according to the customer's preferred frequency and delivery means.

THE PRIMER SHOP acts as a "genetic filter"—scanning through 100s or 1000s of products/services available in the market—in order to recommend to a customer the products/services that are best suited depending on his/her genetic profile. Therefore, THE PRIMER SHOP customer has confidence that he/she is making an optimum purchase, whilst retaining freedom of choice as he/she will make the final product selection based on personal, i.e. non-genetic, preferences.

THE PRIMER SHOP provides a platform that allows partner companies to reach individual customers of THE PRIMER SHOP. These partner companies can have space on the virtual "shelves" of THE PRIMER SHOP, e.g. by means of a "click-through" service. Alternatively, partner companies can benefit from a web browser add-in (plug-in) that helps customers during purchases made directly from the partner companies' web portals.

Applications of THE PRIMER SHOP service model extend beyond the examples provided for human health and lifestyle, and can be applied to any living organism, including animals, plants, microbes, and fungi. For example, information may be sought in connection with a pet's lifestyle, nutrition and pedigree history, fertilisers for a specific tree, or microbes in the gut. Such tests may be carried out for wellbeing, allergy risk, fitness, nutritional supplements, agricultural production, environmental control/investigation, etc.

Privacy must be a key priority for the service and its customers. Therefore, the service safeguards its customers' confidentiality by not disclosing primer sequences and genotypes that are being tested.

EXAMPLE

Consider a customer expressing the lifestyle concern; "do I need vitamin D supplementation?". THE PRIMER SHOP offers in its catalogue a primer XX, with sequence:

```
                                       SEQ. ID NO. 1
ATCTCTGTCTCTTAATTATCTCACA[A/C]AGCCAGGTATTTTTATTGT
TAGCT.
```

This primer maps to the GC gene (Group-Specific Component; Vitamin D Binding Protein)) and can analyse for the SNP Rs2282679. The Rs2282679 (A) allele is considered the normal allele and is associated with zero risk of vitamin D deficiency, while the Rs2282679 (C) is associated with increased risk of vitamin D deficiency. An individual may a) carry two Rs2282679 (A) alleles and have no increased predisposition to vitamin D deficiency, b) carry a Rs2282679 (A) allele and a Rs2282679 (C) allele, having a 1-fold increased risk of having somewhat lower vitamin D levels, or c) have two Rs2282679 (C) alleles and have 1.5-fold increased risk of vitamin D deficiency. Instead of providing all the above information to the client, THE PRIMER SHOP approach is as follows.

The customer selects primer XX that can help answering the lifestyle concern; "do I need vitamin D supplementation?". However, the actual gene that will be screened and the sequence of the primer are not disclosed to the customer nor are they sent over the Internet at any stage, not even in encrypted form. This is required as any storage of genetic information, outside of THE PRIMER SHOP, represents a security risk. [NB. data stored at a customer's computer device is potentially at the greatest risk due to the prevalence of malware that allows attackers to gain access to private data.] The customer is merely sent a test kit including the appropriately prepared DNA test module, with a memory of the test module storing the module reference ID. At this stage, THE PRIMER SHOP deletes all information related to the customer's genotype including the summary report (the module reference ID is stored in a database, mapped to the primers on the module and their locations, but this is not associated with any customer identity). THE PRIMER SHOP retains only the customer's basic subscription related data and, optionally, his or her public key in order to allow it to decrypt data subsequently sent by the customer and encrypted with the customer's private key.

Similarly, the precise details of the test performed using the primer XX are not disclosed at any stage of the service, in order to ensure maximum privacy. Only the data generated by the primer XX, the test location, and the module reference ID are sent online to THE PRIMER SHOP. The analysis returned by THE PRIMER SHOP will not disclose his/her alleles or the genotype, but only the interpretation of the results, e.g. you are/you are not at high risk of developing vitamin D deficiency and therefore, you do/don't require vitamin D supplementation (i.e. an answer to the initial question/concern). At this stage, if the customer is at risk of developing vitamin D deficiency, he/she will be presented with a range of vitamin D supplements, containing suitable concentrations of vitamin D (e.g. 0.01 mg daily), to choose from, such as Mum's Ddrops® in liquid form, Boots™ Vitamin D tablets, Solgar™ Vitamin D3 400IU softgels or tablets, SimplySupplements™ Vitamin D 400IU etc. Furthermore, this interpreted information is sent from THE PRIMER SHOP to the customer in encrypted form to ensure that even this data is kept as secure as possible.

As noted above, the summary report provided to the customer may include product or service suggestions. Where the report is displayed in a web browser of the customer's computer device, the customer may be able to select a product or service by clicking on a link, whereupon an order may be made through THE PRIMER SHOP's purchasing portal or via a partner's portal (i.e. a click-through process). Order information may be secured using the customer's public/private key pair.

The client's computer device does not retain the test results. Rather, it retains only the summary report and the genetic filter code(s) (whilst the genetic filter codes have been decrypted to a first level using the customer's private key, they remain encrypted with THE PRIMER SHOP's private key). By sending the (encrypted) code(s) to THE PRIMER SHOP, where they are decrypted using THE PRIMER SHOP's private key, THE PRIMER SHOP is able to repeat the analysis using, for example, any newly acquired data (e.g. genetic/scientific or newly available products and services) and provide an updated product and/or service selection to the customer. Once again, after the updated report has been prepared and sent to the customer, THE PRIMER SHOP deletes all genetically related data including the report and the genetic filter code(s).

Figure 3:
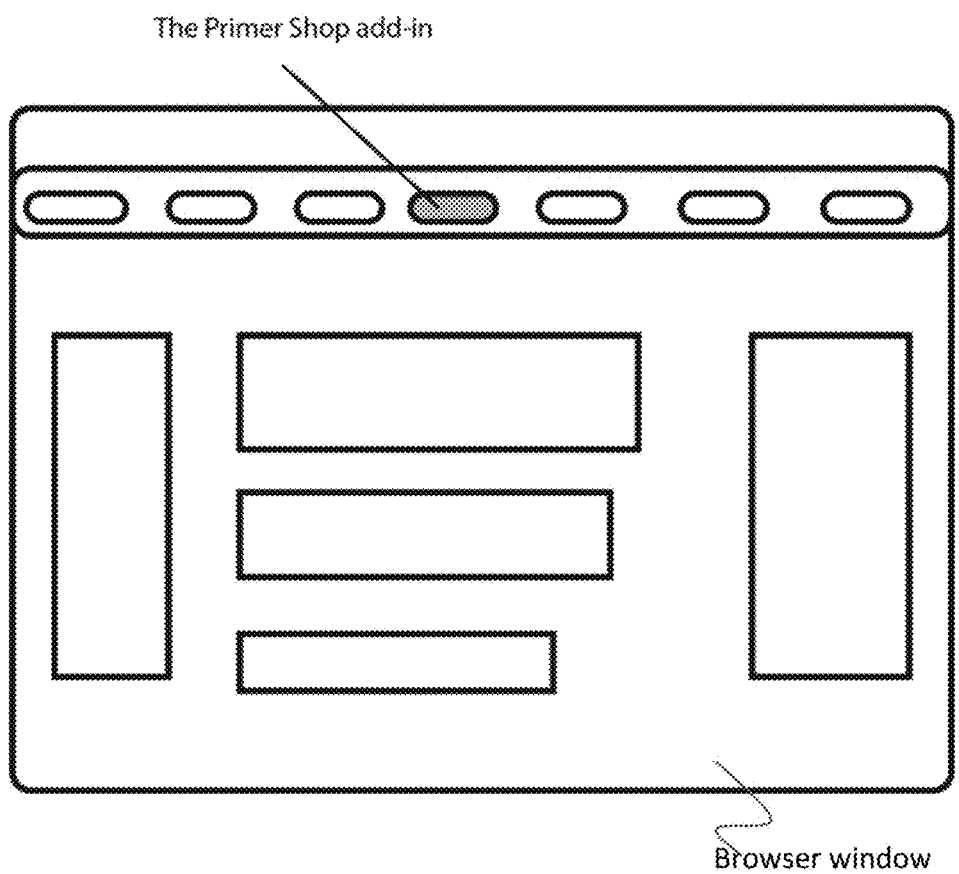
Figure 4:
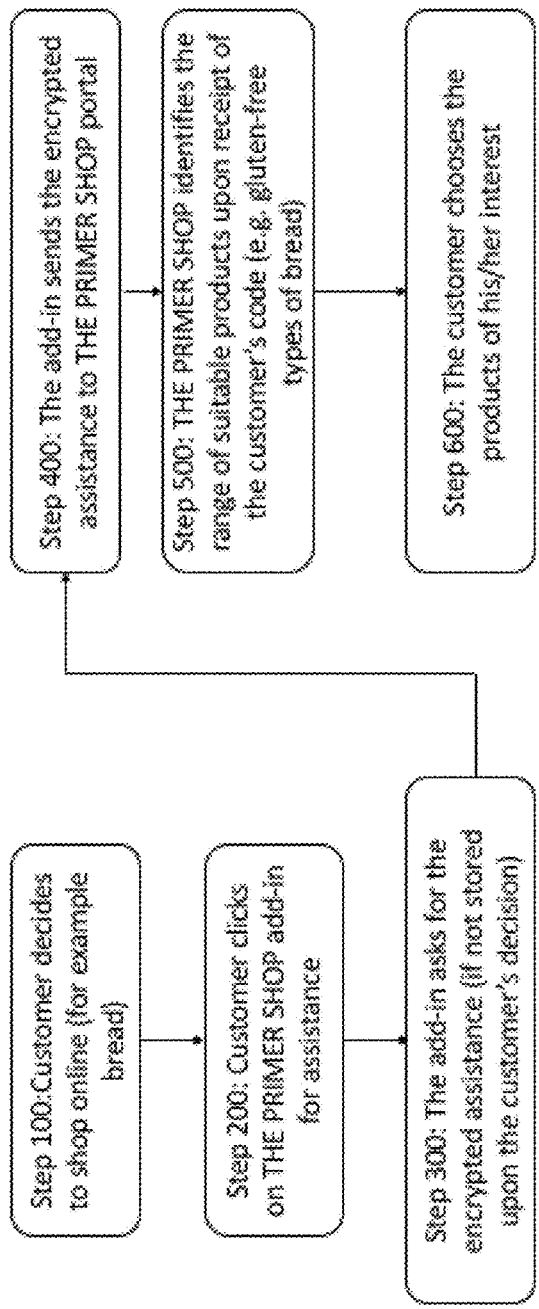
FIG. 4 is a flow diagram illustrating the use of the new browser button to assist purchasing decisions.

An alternative approach to facilitating product or service purchasing involves THE PRIMER SHOP providing to the customer's computer device an Internet browser add-in or plug-in (or a similar component for a dedicated interface that a product provider may have, e.g. an app for AMAZON™). This is illustrated schematically in FIG. 3, and the operating procedure in FIG. 4. The plug-in has access to the previously received genetic filter code(s) stored at the customer's computer device. Once installed into the Internet browser, the customer opens his or her web browser to begin shopping online—step 100—and clicks on the TPS button for add-in assistance—step 200. The plug-in accesses the customer's encrypted genetic filter code(s), and sends this to THE PRIMER SHOP together with identity of the accessed website—Steps 300/400. NB. This information is sent anonymously preventing THE PRIMER SHOP from associating the genetic filter codes with the customer. THE PRIMER SHOP decodes the genetic filter codes with its private key and returns to the customer's plug-in, information that it can use to filter the information presented to the user in the browser window, for example a filtered list of products—Step 500. [This information can again be sent encrypted with the customer's public key (e.g. sent with the customer request).] For example, the plug-in may "grey-out" certain products or services that are deemed unsuitable for the customer, and the customer can proceed to choose a product from the filtered selection—Step 600. In this way THE PRIMER SHOP acts as a "gateway" to the partner company's website.

Prior to applying the filter, the plug-in may initiate a customer authentication procedure, requiring the customer to authenticate him or herself to THE PRIMER SHOP server. THE PRIMER SHOP can then track purchases made when the filter is applied, e.g. to reconcile charges made by THE PRIMER SHOP to the partner company. This authentication and tracking procedure is not associated with the procedure described in the preceding paragraph—i.e. the sending of the genetic filter codes to THE PRIMER SHOP. It will be appreciated that the use of this approach leaks no genetically related information outside of the customer's computer device. Specifically, no data is leaked to the partner company from which purchases are made.

Figure 5:
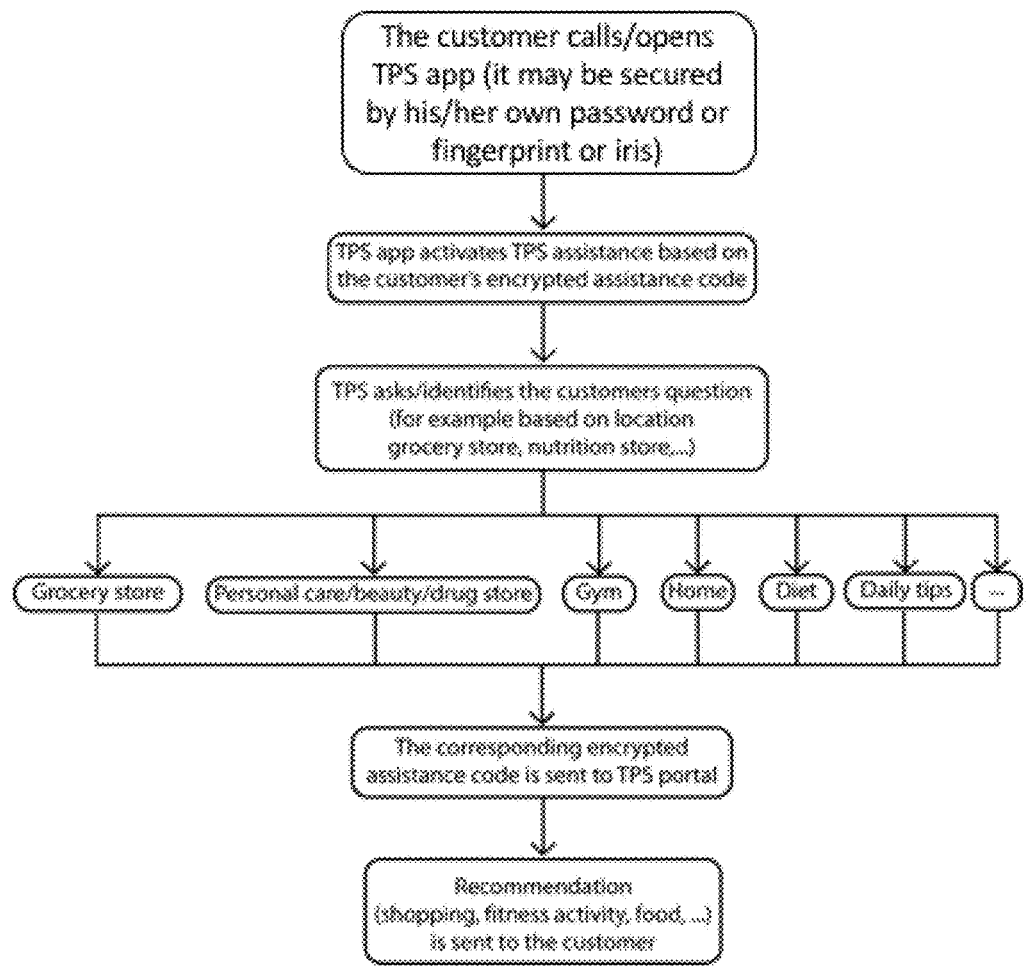
FIG. 5 illustrates a procedure for providing a customer with product/service recommendations and utilising a dedicated app.

THE PRIMER SHOP may provide its customers with an application ("app") that can be run on smartphones and other mobile devices. This tool can be used as a product selection or lifestyle assistant for "on-the-spot" in-store or online purchases. The app will allow the user to scan product barcodes in-store, retrieve information associated with the genetic filter code(s) retrieved from THE PRIMER SHOP, and filter products by narrowing down selection based on the user's genetic filter code(s). Again however, the app only has access to the encrypted genetic filter code(s) and no genetically related information is leaked. FIG. 5 illustrates the operation of an exemplary app.

Where product manufactures/providers have a partner relationship with The Primer Shop, the products may carry a "THE PRIMER SHOP Quick Response code" (TPS-QR code). The QR code contains, in encrypted form, a list of the genetic filter codes relevant to the specific product to which it is attached. [The TPS-QR code is encrypted in accordance with the policy of THE PRIMER SHOP of not disclosing the actual primers' sequences and the actual genotype of its clients.] This allows a suitable app, installed on the customer's computer device to send a query to THE PRIMER SHOP including the QR code data and the encrypted customers genetic filter codes. Again, THE PRIMER SHOP is able to return data that allows the app to provide product filter data, e.g. advice concerning the suitability of the product and/or suitable alternatives.

The app is an intelligent, interactive and intuitive assistant. For example, when the customer is in the premises of a grocery store, it may remind the customer of the type of products he/she needs to buy. When the customer is in the gym, it may remind him or her what sort of exercises are necessary (possibly being linked with some mechanism—e.g. accelerometers, motion sensors, etc.—provided within the device to track actual exercises performed).

Figure 7:
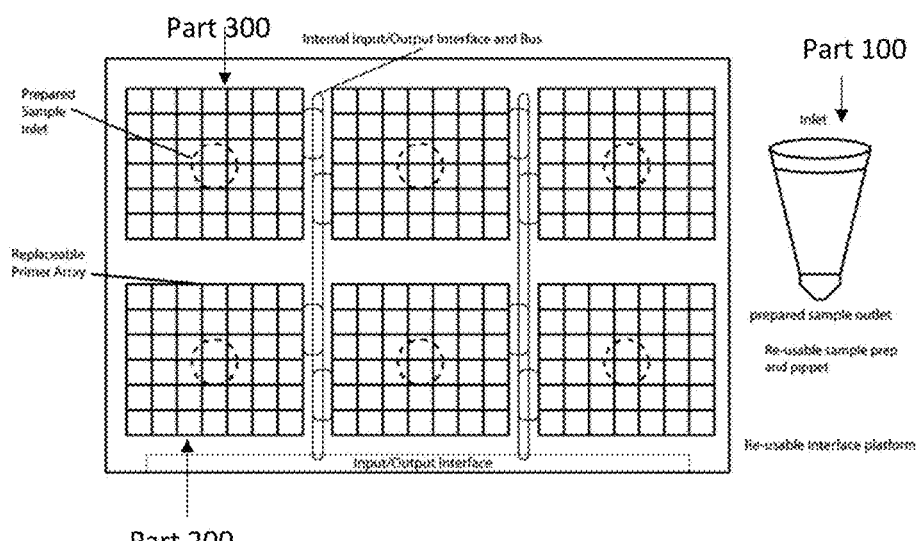
FIG. 7 illustrates schematically a semi-disposable DNA test kit.

THE PRIMER SHOP may provide customers with a two-part test module have a first part configured to be connected to the customer's computer device, e.g. via a USB connection. This first part is further configured to receive, via a plurality of sockets, a plurality of disposable sample parts. The sample parts include the chosen primers, and means for receiving the genetic material to be analysed. Sample parts are activated individually, e.g. after insertion into the first part. This approach allows tests to be carried out in parallel, but with each starting at a different time. This is illustrated in FIG. 7 which shows the sample preparation kit 100, together with the first part 200 having an Input/Output interface for connection to the customer's computer device. The first part 200 has sockets for connecting six disposable sample parts 300.

Figure 8:
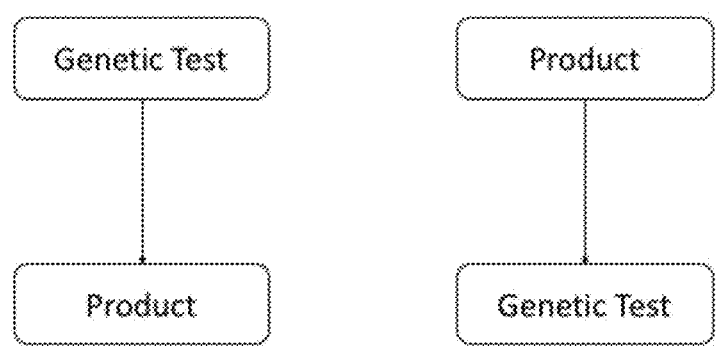
FIG. 8 illustrates two approaches to providing personalised genetic-related advice to customers.

FIG. 8 illustrates schematically two approaches to providing personalised genetic-related advice to customers. This can take as a starting point genetic information and, based on this provide advice relating to specific products (or services etc), or can take as a starting point a product (or service etc.), such as a brand of chocolate bar, and then recommend a genetic test.

Figure 9:
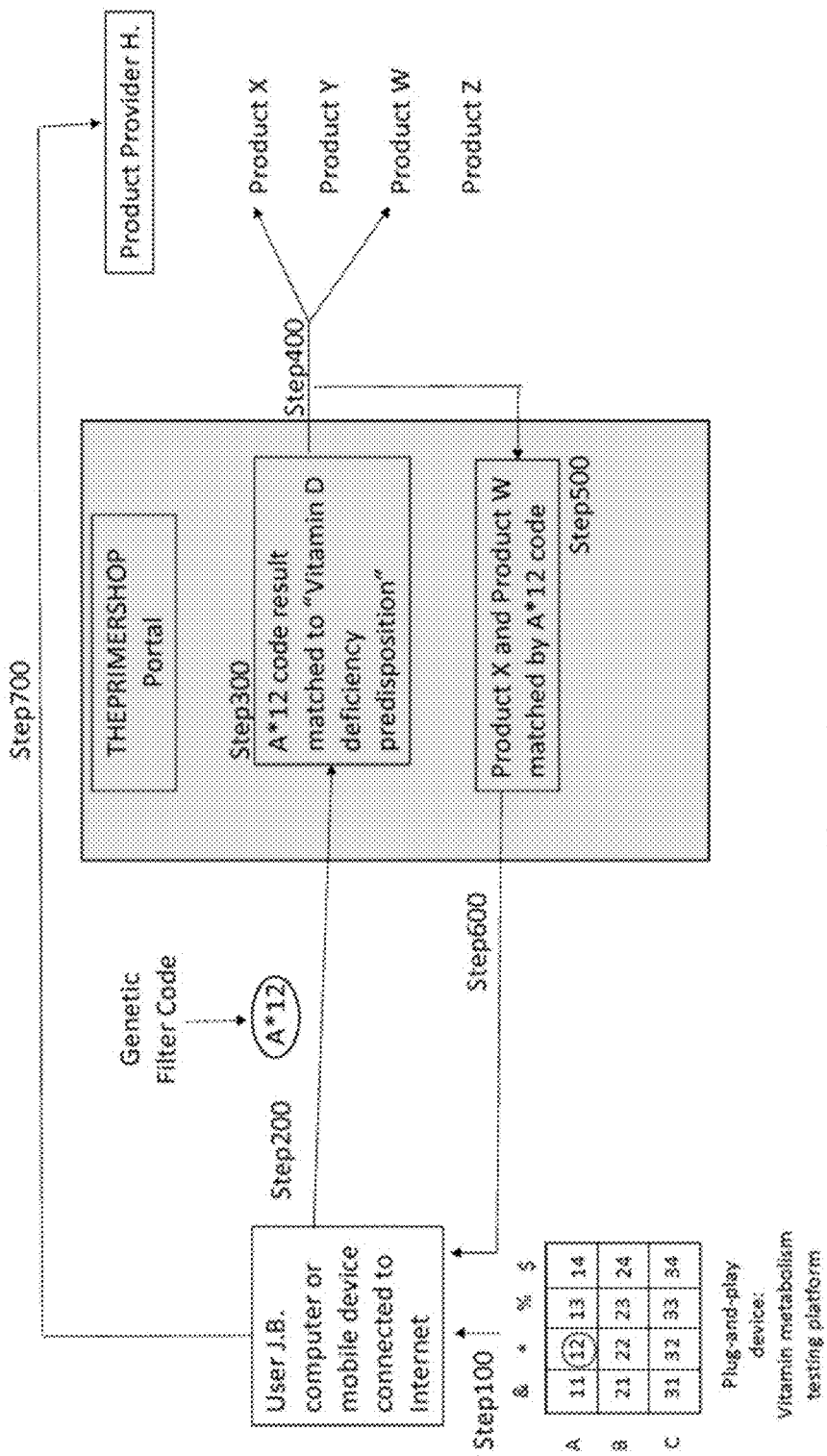
FIG. 9 illustrates schematically an end-to-end product ordering service.

FIG. 9 illustrates schematically a product ordering service utilising the method and apparatus described above. This presents the following steps:

Step 100: The user purchases a test-kit plug-and-play platform, applies biological sample and connects via a computer or mobile device to the Internet Step 200: Customer's genetic filter code sent to THEPRIMERSHOP portal Step 300: Genetic predisposition determined Step 400: Product mapped according to the customer's genetic filter code Step 500: Product recommendations retrieved by THEPRIMERSHOP portal and matched back to the customer's genetic filter code Step 600: Product recommendations sent back to the customer Step 700: Customer chooses the product of his/her choice and proceeds to the purchase Steps 100 to 700 are being performed via secure server link by using private and public key system encryptions.

Here we are proposing a novel method/apparatus to apply breath analysis into lifestyle management, in particular selection of suitable nutritional products. For example, we may look at 13C-octanoate release rate which is correlated with the absorption of medium-chain fatty acids. Accordingly, the person may be advised to temporarily select lower-fat products.

Another example is Lactose intolerance and maldigestion. While the genotypes can give an indication of possibility of lactose intolerance, breath analysis on $H_2$ and $CH_4$ can further clarify whether the symptoms are around lactose intolerance or maldigestion.

Similarly, breath analysis can indicate of the activity of the microbiome inside the stomach. When digesting food, it is not just our body organs that are involved; there are hundreds of thousands of bacteria that are involved too. Therefore, knowing about the condition of the microbiome can help understanding how the nutrition intake can be adjusted accordingly.

Figure 30:
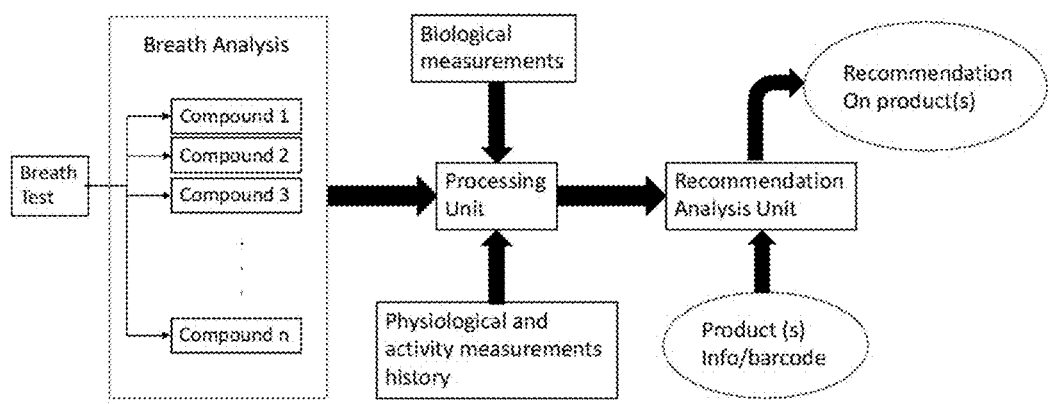
FIG. 30 is a flow diagram illustrating a system for product recommendation based on breath testing.

FIG. 30 gives an overview of a system/method that helps the user to decide (on product selection or activity) by giving recommendations. Based on the level of individual or pattern of a group of biomarkers (the compounds in breath), it can identify/predict the possible outcomes of each decision. Therefore, recommending which may have a potentially better outcome than the others. In this system, historical analysis may also be taken into account to show how the metabolism behaviour has changed.

The biological and physiological and activity measurements may consist of a variety of information and parameters. For example, it may take into account the person's genetic background, epigenetic analysis, genetic expression, hormones and vitamins levels, physical activity and exercises, body weight and height, glucose levels, etc. It may also include the historical breath test results.

For example, a person might be a carrier of a Single Nucleotide Polymorphism (SNP) which may eventually result in the person becoming a diabetic. Monitoring the acetone level change in the breath, can indicate if the person is at risk and needs to take more control of his/her diet, or perhaps otherwise indicate that he/she is doing alright and the genetic variation has remained silent.

Figure 10:
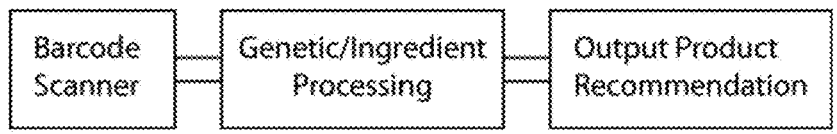
FIG. 10 illustrates functionality for providing product recommendations.

Reference has been made above to the use of a smartphone with barcode scanning functionality to identify products and provide product recommendations based on a user's personal genetic information. It is proposed here to implement a similar functionality in other "wearable" device types. Of particular interest is the implementation within a wristband-type device. FIG. 10 illustrates schematically one such device where the functionality is implemented within a module coupled between, or formed integrally with, a pair of wrist straps. It will be appreciated of course that the module may be configured to attach, e.g. snap-fit, to an existing wristband of a watch, bracelet, fitness tracker band, etc. As will be described below, the module (or "wristband" as it will be referred to hereinafter) is configured to communicate wirelessly with a computer device such as a smartphone, with the smartphone in turn communicating, e.g. via a wireless data network, with (cloud) servers operating a backend date service.

In very general terms, the wristband is constructed and configured to maintain data relating to current products including product codes and respective product recommendations determined using personalised genetic data, preferably, though not necessarily, of the wearer. These product codes correspond to machine readable codes such as 1D or 2D barcodes (e.g. UPC/EAN), QR, ISBN, PDF417, Data Matrix etc, etc. The wristband is provided with a product code reader such as a barcode reader for reading product codes printed or otherwise provided on products intended for purchase or use. One such example of a product code reader is a camera, with associated processing circuitry for recognising an imaged barcode and for converting the barcode into a digital code. This wristband further comprises processor circuitry for using the read product code as a look-up key in the database of product codes and product recommendations in order to retrieve the product recommendation. The wristband is also provided with a means for providing an indication of the determined product recommendation to the wearer. This could include a vibration motor which provides a vibration signal. Of course, the means may alternatively or additionally provide a visual or audible signal to the user.

In a typical use scenario the wristband may be loaded, via the smartphone, with product codes for grocery items available within his or her geographic region, e.g. the United Kingdom. The wristband is also loaded with respective product recommendations for the wearer (or at least as many as are available and/or useful). These recommendations may have been determined by the smartphone by applying the TPS codes for the wearer with product data downloaded from the cloud. For example, the smartphone may download the product codes from the cloud together with details of product content. For a particular product having say a high fat content, application of the TPS codes may indicate that the product is not recommended for the wearer and as such the product, or rather product code, is associated with a relatively low product recommendation. The recommendation could be a simple yes or no or may be a value, e.g. between 1 and 10. The wearer may further personalise the service by manually inserting lifestyle preferences (e.g. sugar or calorie intake reduction goals etc), e.g. using a management interface of the smartphone.

When the wearer enters a grocery store, the wristband will already have been loaded with product codes and product recommendations so no connectivity, e.g. to the cloud or to the smartphone, is required. The wearer identifies a product of interest and scans the product barcode. He or she is given immediate feedback, e.g. by a short vibration, that the product is recommended. If the product is not recommended, a prolonged vibration may be generated. Based on this feedback the client is lead, or "nudged", towards a healthier and/or more appropriate choice. If the display on the wristband is suitable, the wristband may provide an indication of a more suitable product if one is available within the database. The wristband may also communicate with the wearer's smartphone at this point, if a connection is available, to provide such an indication and/or to provide additional product information.

The wristband may be further configured to receive confirmation that a scanned product has been purchased, and to log this data for future use. An indication may be given by the wearer pressing a button on the wrist band, tapping on the module, shaking his or her wrist, etc. A mechanism may also be provided to allow removal of a product from a purchase list, e.g. due to a change of mind. Alternatively, purchase data may be provided to the smartphone by scanning a store till receipt, or by some interaction with the cloud whereby the store transfers purchase details to an account which can be accessed by the user's smartphone.

Data identifying purchase may be fed back to the mechanism that determines the product recommendations for the wearer. For example, in the case that the wearer's genetic information results in a generally high or positive recommendation for a given product, if the wearer is determined to be consuming a large amount of that product or of certain of its contents, e.g. fat, the product recommendation may be reduced to nudge the wearer to reduce consumption.

Although genetic information is of course personal, it is recognised that many product purchases, especially concerning groceries, are intended for consumption by a group of people, e.g. by family and/or friends. It may therefore be desirable to allow the database in a wristband to be updated to reflect the product recommendations for a group of individuals. This may be achieved by merging the data, e.g. by averaging the product recommendations across the members of a group, and/or by taking into account certain product or ingredient intolerances or allergies. This is considered in more detail below.

A more sophisticated service may be able to take account of data recorded in a product barcode including, for example, product ingredients, nutritional content, % RDA (Recommended Daily Allowance) or % RI (reference intake) or % NRV (nutrient reference value), allergen information, product features, functions, the origin of product ingredients, manufacturing procedures, product mileage, organic certifications etc. This data can be used to adjust the product recommendations.

Figure 11:
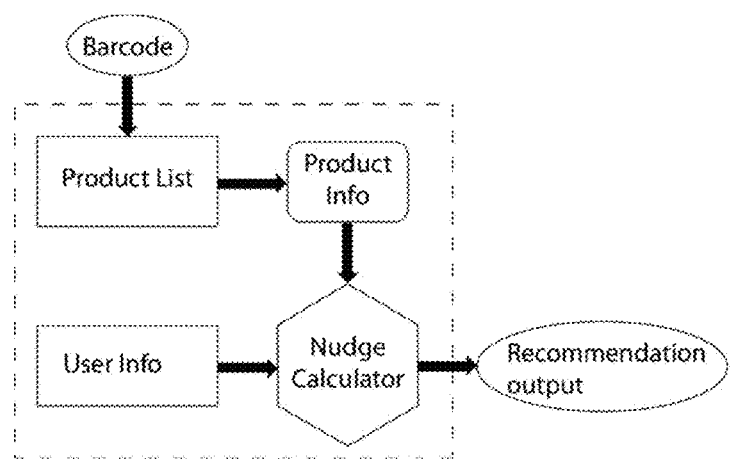
FIG. 11 further illustrates the functionality of FIG. 10.
Figure 12:
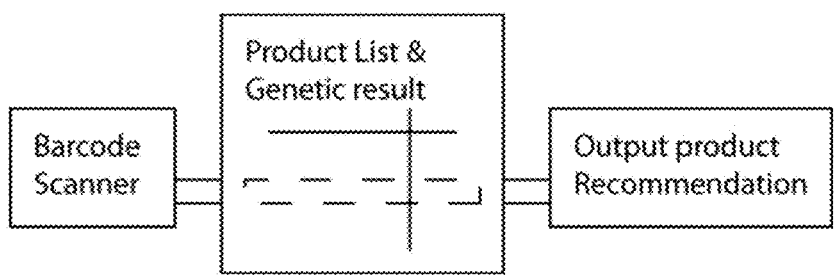
FIG. 12 further illustrates the functionality of FIG. 10.

FIG. 10 gives an overview of the system application. The wearer scans the product barcode and wristband outputs a recommendation about the product. This can be implemented in different ways. The analysis for giving a recommendation can be done locally (FIG. 11) or it can be pre-loaded to the device (FIG. 12) as discussed above. In both scenarios, the list can be updated, for example through a cloud-based server (FIG. 13), directly or via the wearer's smartphone.

FIG. 14 shows an example schematic block diagram of the wristband structure. The components include:

A barcode scanner such (e.g. a CMOS imager) that scans the product barcode.

A random access memory that stores the read barcode

The Barcode Memory (database) that contains a list of all product barcodes with their related personalized results, i.e. product recommendations.

(A memory storing the genetic information (the genotyping test result, e.g. TPS codes) of the user in case of local processing.)

As has been considered above, the system helps the user in identifying the products that are not suitable and are better to be avoided. By further refinement, for example taking into account bio/physiological conditions of the user, the system can encourage the user towards products that are potentially more suitable for the user. FIGS. 15 and 16 illustrate this concept. The Figures illustrate a system which rates products on a scale of "1" to "7", where "1" is highly recommended and "7" of not recommended.

Figure 17:
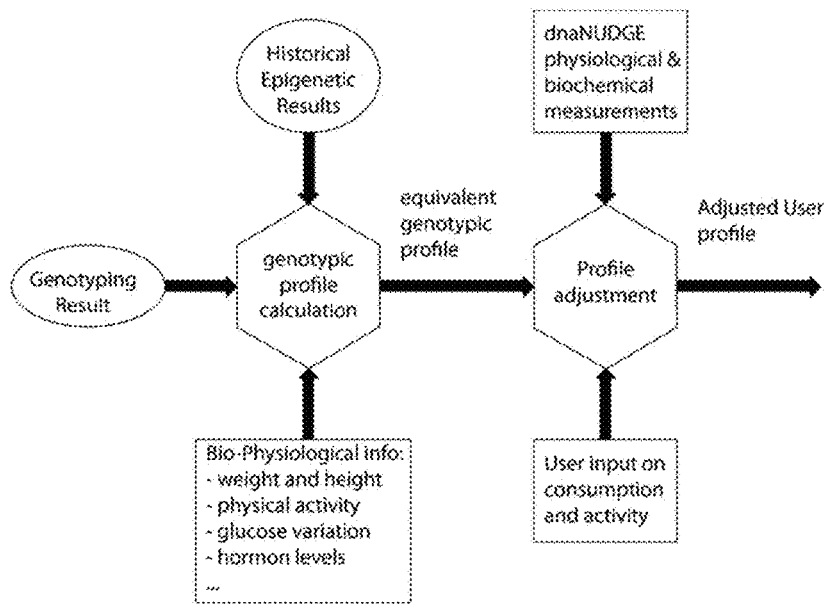
FIG. 17 shows a scheme for deriving product recommendations utilising various information types.

As has already been alluded to, personal genetic information may be supplemented with additional information, such as user preferences, in order to determine product recommendations. Some of this information may be taken into account when determining the TPS codes or may be used together with the TPS codes to determine product recommendations. FIG. 17 illustrates schematically a "holistic" approach to the determination of product recommendations, where the results output (on the right of the diagram) are the product recommendations. Of particular significance here are epigenetic information and sensed data.

Epigenetic Data

It is known that epigenetic data for user can identify changes in the user's physiology due, for example, to changes in the user's lifestyle and diet. By performing epigenetic tests on the user at certain time intervals, product recommendations may be changed/refined. For example, epigenetic data may indicate, in combination with data collected relating to product purchases, that the purchase or non-purchase of certain products has resulted in a positive health benefit for the user. The system may take this into account when updating the product recommendations, e.g. where the user was previously not recommended to consume a high fat product, the recommendation for this product might be nudged up to indicate to the user that some limited consumption is now less harmful.

Epigenetic data may be obtained, for example, by analyzing a sample of a user's genetic material (obtained using a cheek swab, saliva sample, blood sample etc) or transcription data by analyzing a user's mRNA.

Sensed Data

The proposal here to incorporate the system into a wearable device such as a wristband makes possible the use of sensed data such as biochemical and physiological/environmental data. In particular, the device may be configured to monitor the wearer's heart rate and hence determine the rate at which the wearer burns calories. This sensed data can be used to modify the product recommendations in any of the short, medium or long term. For example, if the system detects that the wearer has just been extremely physically active, a drink with a high sugar content may be recommended. Thereafter the recommendation for that drink returns to the long term value.

Figure 18:
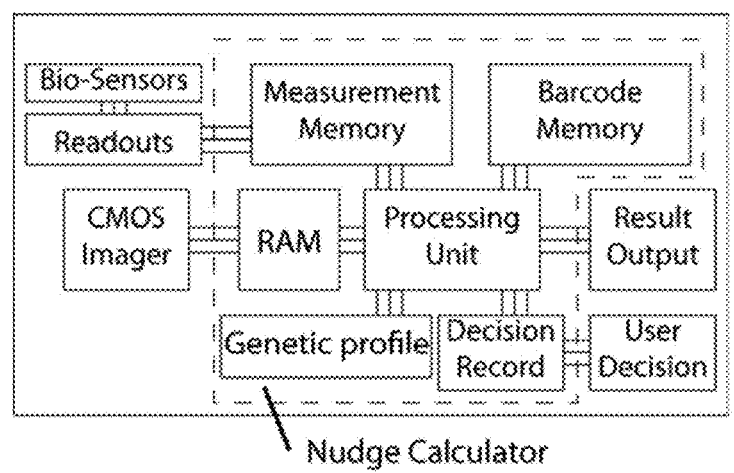
FIG. 18 illustrates schematically components of a further wearable device.

FIG. 18 illustrates schematically a device architecture that enables a sophisticated calculation and recalculation of product recommendations. The system includes biosensors for measuring biochemical and bio-physiological data of the wearer, and circuitry for combining this with the genetic data directly or indirectly. Of course, certain of the circuitry may be implemented in the smartphone and/or cloud.

Figure 19:
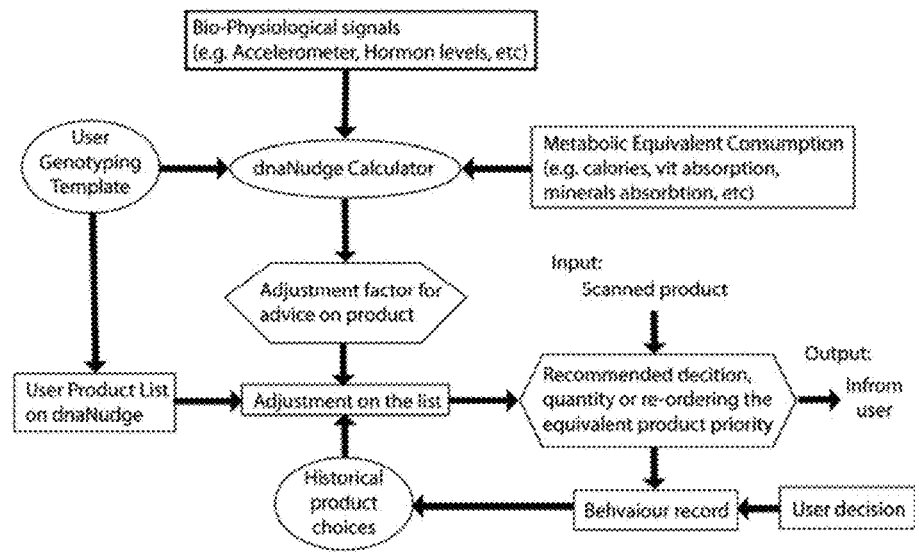
FIG. 19 shows a further scheme for deriving product recommendations utilising various information types.

FIG. 19 shows a still more sophisticated system which takes account of genotypic, epigenomic, biological, physical, and behavioural characteristics of the user. An example of a biochemical sensor may be a sensor, placed on the underside of the wristband, that uses microneedles to measure the wearer's glucose, cholesterol, or hormone levels. The device may additionally be provided with environmental sensors, e.g. a UV sensor. The results generated by such sensors may also be fed into the determination and/or use of the product recommendations.

Given the current popularity of fitness bands for monitoring activity, health, etc, it would be of great interest to incorporate the system described here into such a fitness band. Of course, fitness bands already include some of the sensors proposed above. There may be some synergy between the components of the fitness bands and the new functionality. For example, optical components of a pulsed-light heart rate monitor may be incorporated into a barcode scanner to avoid the need for an additional light source and/or light detector.

The device may be enhanced to include a sighting or targeting means to aid in locating and capturing a barcode to be scanned. For example, the device may project a light spot onto a central point of the scanning area. The user locates the light spot onto the centre of the barcode. The device may have a means for automatically recognising a barcode and capturing the code, or it may require the user to press a button, or possibly provide a voice command.

By means of a management application, e.g. in the wearer's smartphone, the wearer may input data relating to personal allergies, e.g. a nut allergy, or an intolerance. These may be factors that are not picked up by a genetic test and which are therefore not reflected in the TPA codes.

It is desirable to maximise battery life in the device, and this can be challenging given possible high power demands of scanning. The device may therefore be configured to operate in a low power sleep mode and a relatively high power active mode, the device being operable in the sleep mode to recognise a generic product code and cause a switch to the active mode. Thus, for example, the imaging system of the device may be able to recognise a barcode without necessarily reading the code, e.g. it is merely able to identify a set of black and white lines. Only when such a pattern is detected does the device switch to a high power mode in which the barcode is read, decoded, and a recommendation determined and presented.

Figure 20:
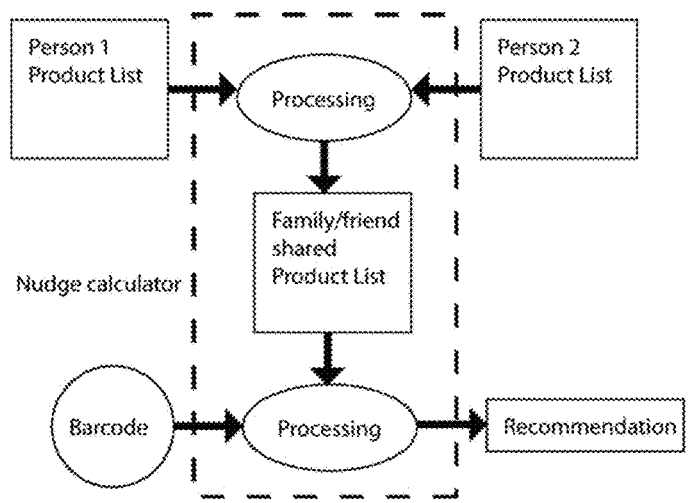
FIGS. 20 and 21 illustrate alternative schemes for providing product recommendations for a pair of individuals.
Figures 21, 22:
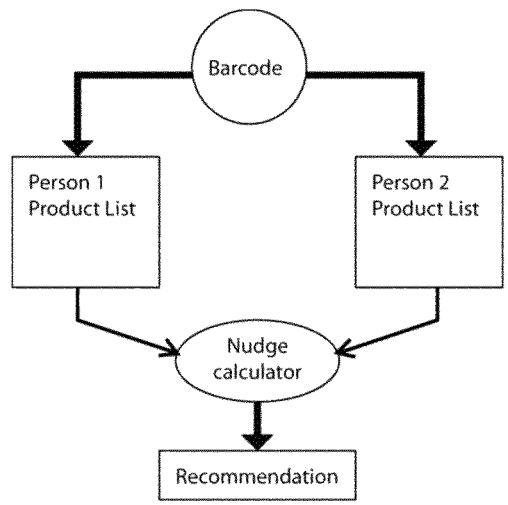
FIG. 22 further illustrates a scheme for merging user data.

Returning now to the proposal that product recommendations may be evaluated across a group of individuals, as has already been noted, shopping is not necessarily always personal, but may be carried out for a family/household. The shopping basket is dominated by products that all the people in a house use. In this case, the system can determine an optimum product list, or tell the user whether a particular product is suitable for all in the house or if it is in particular avoided by a member. FIGS. 20 and 21 show how the system can help sharing product lists and creating an optimum common list of products among people sharing a common basket. By way of example, as shown in FIG. 20, the product recommendation lists for two individuals may be merged to produce a single list that is downloaded onto the device of the person that is doing the shopping. Alternatively, as shown in FIG. 21, individual lists may be loaded onto the shopper's device and the lists examined and the results combined to determine a product recommendation.

FIG. 22 illustrates an example of how a calculation can help identifying the optimum product choice from a number of biscuit brands for a group of four individuals. Each biscuit for each person have been given a product recommendation (score). The lower (negative) the score is, the less suitable it can be considered. The higher the score is, the better the biscuit matches the user's template. Now, in order to find the optimum biscuit, the overall score is calculated. The biscuit that gives the highest score is the product of choice. However, the biscuit chosen should be the one that does not have a negative score for any of the four individuals. In this example, Biscuit 2 is recommended.

Figure 23:
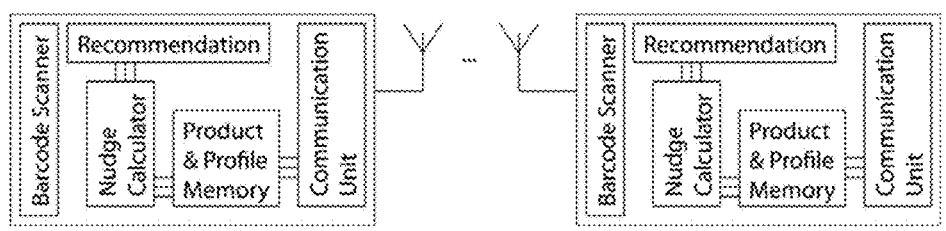
FIG. 23 illustrates two wearable devices configured to share data.

This concept of sharing can be implemented in different ways. Considering the wearable device (for example a wristband), a wireless link between two or more devices can allow the product list and profile transfer (sharing). This link may be, for example, NFC, infrared, Bluetooth, Wi-Fi, etc, and be activated when the peer wristbands get close to each other or touch each other, i.e. "bump" together. Some prior approval may be required to avoid accidental sharing, e.g. a given user may add other users to his or her contact list using the smartphone management application. A possible implementation is illustrated schematically in FIG. 23. Of course, to take account of the fact that a user may be shopping for different groups, different combinations of individuals within a group, of for him or herself alone, the system may be configurable. For example, the wearable device may allow the wearer to select a combine option and, if so, to select the individuals to which the combination relates.

Because the device is making use of personalised data it may in some circumstances be desirable to be able to identify the wearer. Consider for example the case where a family share a single device. In order to allow the device to select the correct product recommendations for that individual, the device may be configured to identify the individual based on sensed data such as physiological date, motion data (e.g. a particular pattern of movement).

In some cases a user may not have access to product recommendations for another individual for whom he or she is shopping, either because that information has not been shared or because the other individual has not obtained the data (e.g. has not subscribed to the service). If the other individual is a genetically related family member, it may be useful to provide a filtering of the product recommendations based upon genes that are known to be hereditary. Product codes received from the smartphone for the wearer may be marked to identify those that are associated with some hereditary traits. Recommendations may only be provided for those products provided with the marker. As with the sharing option, the device may be provided with some means to switch this hereditary-based selection on and off The system can be implemented as a wearable, carrying the users' personalised product lists with barcodes. When the user scans a product barcode, the system can tell the suitability of the user's choice. The user may be notified of the outcome in different ways. For example, a colour light can be projected on the product barcode (e.g. green showing suitable, red warning of its unsuitability, and amber to let the customer know that while suitable, there are actually better ones for him/her); the screen colour might change, or it might vibrate.

Figure 24:
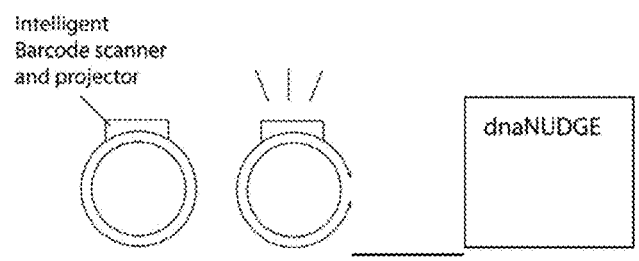
FIG. 24 illustrates schematically a number of wearable device embodiments.
Figure 24:
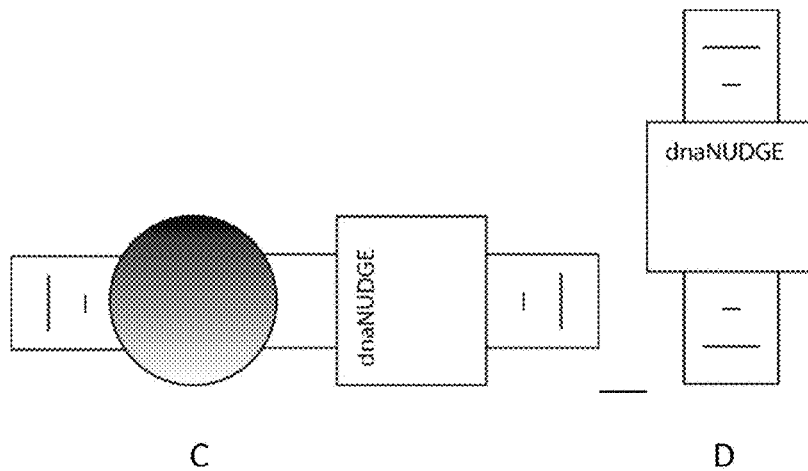

FIG. 24 illustrates four alternative embodiments of a wearable device implementing the key functionality described above. These embodiments are: A. a ring or keyring; B. a standalone unit suitable for example for carrying in a purse, bag or pocket; C. a module for attachment to a wristband of a watch; D. a module integrated into a wristband.

Figure 25:
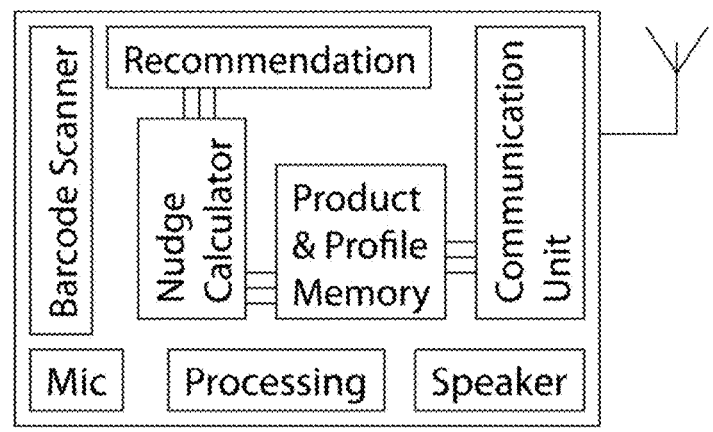
FIG. 25 illustrates various components of a wearable device.

FIG. 25 illustrates schematically a device with an audio interface including a microphone ("Mic") that allows the wearer to use voice commands to control the device. This would enable the wearer to interact with the device to, for example, confirm that a scanned product is being purchased. Other ways for the wearer to interact with the device can include:

Tapping on the screen (for example, a single tap to choose the scanned product, a double-tap to refuse to take the product;

Swapping fingers over a screen; and

Blocking the scanner camera, e.g. by raising fingers/hand.

Assuming that the device includes some motion detection mechanism, e.g. accelerometers, the device may track the hand movement for identifying a purchasing decision; i.e. whether it is toward a basket or toward the shelves. The device may alternatively configured to recognize particular hand gestures, e.g. the shake of a hand etc and associate these with a purchasing decision.

The device may use body movements to identify when the user is interested to a scan. For example, when the hand in a certain position, it might automatically turn on the scanning system. The device may alternatively use a location service module, for example a GPS, to turn on automatically when the user enters a store. Location information determined in this way may also be helpful in switching on or off certain parts of the product list. For example, when a wearer enters a particular store, the product list may be filtered to use only products available in that store. This will prevent unavailable products being offered to the user (if such an option is enabled).

Figure 26:
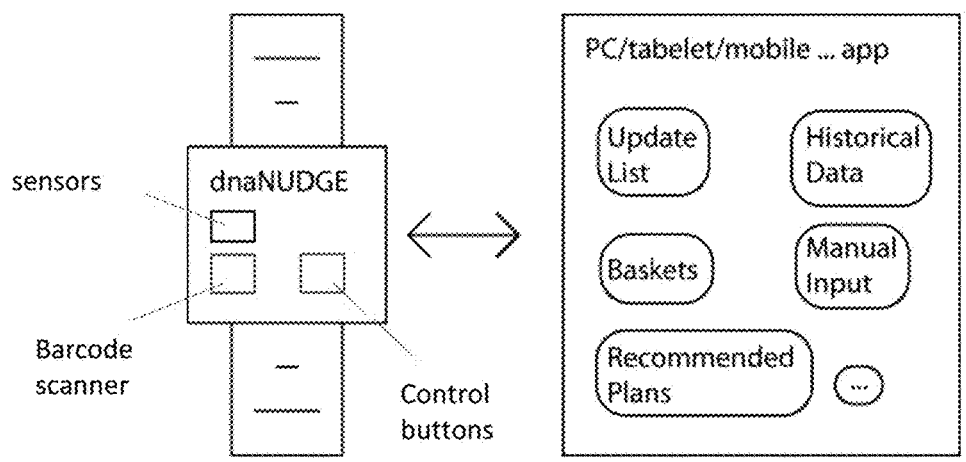
FIG. 26 illustrates a wearable device and a computer device having a management app for managing the wearable device.
Figures 27, 28, 29:
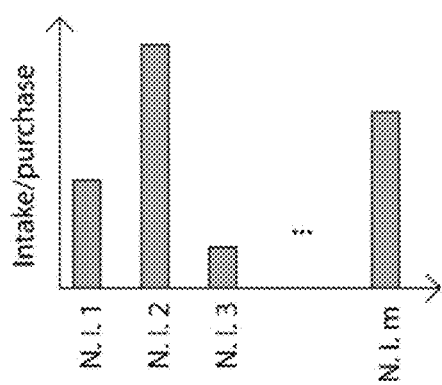
FIGS. 27 to 29 illustrate functions of a management app for managing a wearable device.

System users may have a service account where he/she can use a variety of system features (overview in FIG. 26). For example, scanned product purchases can be loaded into the user's account. The user can then approve if he/she has consumed all/some of the products via some graphical user interface, e.g. on the user's smartphone (FIG. 27). The default/expected amounts can be predicted based on the user's previous values. The user just needs to adjust and/or approve the estimates. The user can have the option to manually enter data (FIG. 28), e.g. using the management application. The application guides the user toward optimum changes, providing an analysis of his or her "performance" (FIG. 29).

It will be appreciated by the person of skill in the art that various modifications may be made to the above described embodiments without departing from the scope of the present invention. For example, whilst an exemplary use of the system and device involves human use, the invention can be applied to animals including pets and horses, plants, fungi, etc. Also, whilst the products may be food and beverages, the invention applies also to other grocery products including detergents and other cleaning products, as well as other products whose suitability depends upon genetic traits, e.g. footwear, glasses, etc.

TABLE 1

| BrandX bar | | |
|---|---|---|
| Nutritional facts | | |
| Serving size | 52.7 g | |
| Calories | 250 | |
| Calories from fat | 110 | |
| Amount per Serving | | % DV* |
| Total fat | 12 g | 18% |
| Saturated fat | 4.5 g | 23% |
| Trans Fat | 0 g | |
| Cholesterol | 5 mg | 2% |
| Sodium | 120 mg | 5% |
| Total carbohydrates | 33 g | 11% |
| Dietary fiber | 1 g | 4% |
| Sugars | 27 g | |
| Protein | 4 g | |
| Vitamin A | | 0% |
| Vitamin C | | 0% |
| Calcium | | 4% |
| Iron | | 2% |

*Percent daily values (DV) based on a 2000 calorie diet
Ingredients

Milk chocolate (sugar, cocoa butter, chocolate, skim milk, lactose, milkfat, soy lecithin, artificial flavor)
Peanuts
Corn syrup
Sgar
Palm oil
Skim milk TABLE 1-continued BrandX bar Lactose
Partially hydrogenated soybean oil
Salt
Egg whites
Artifical flavour

REFERENCES

"The Breath Test That Diagnoses Diabetes" Wall Street Daily, published Thu, Jan. 29, 2015, Martin Denholm, Managing Editor http://www.wallstreetdaily.com/2015/01/29/diabetes-acetone-breath-test/

Michaletz, P. A., Cap, L., Alpert, E. and Lauterburg, B. H. (1989), Assessment of mitochondrial function in vivo with a breath test utilizing α-ketoisocaproic acid. Hepatology, 10: 829-832. doi:10.1002/hep.1840100513

Misselwitz, B., Pohl, D., Fruhauf, H., Fried, M., Vavricka, S. R., & Fox, M. (2013). Lactose malabsorption and intolerance: pathogenesis, diagnosis and treatment. United European gastroenterology journal, 1(3), 151-159.

Jackson, S. J., Leahy, F. E., McGowan, A. A., Bluck, L. J. C., Coward, W. A., & Jebb, S. A. (2004). Delayed gastric emptying in the obese: an assessment using the non-invasive 13C-octanoic acid breath test. Diabetes, Obesity and Metabolism, 6(4), 264-270.

Berg, L. K., Fagerli, E., Martinussen, M., Myhre, A. O., Florholmen, J., & Goll, R. (2013). Effect of fructose-reduced diet in patients with irritable bowel syndrome, and its correlation to a standard fructose breath test. Scandinavian journal of gastroenterology, 48(8), 936-943.

Martins, I. J., Tran, J. M. L., & Redgrave, T. G. (2002). Food restriction normalizes chylomicron remnant metabolism in murine models of obesity as assessed by a novel stable isotope breath test. The Journal of nutrition, 132(2), 176-181.

The volatile metabolome and microbiome in pulmonary and gastro-intestinal disease Marc van der Schee, PhD thesis, University of Amsterdam (2015)

The application of FAIMS gas analysis in medical diagnostics, J. A. Covington, M. P. van der Schee, A. S. L. Edge, B. Boyle, R. S. Savage, R. P. Arasaradnam, Analyst, 2015

A simple breath test for tuberculosis using ion mobility: A pilot study, A. S. Sahota, R. Gowda, R. P. Arasaradnam, E. Daulton, R. S. Savage, J. R. Skinner, E. Adams, S. A. Ward, J. A. Covington, Tuberculosis, 2016

Detection of Colorectal Cancer (CRC) by Urinary Volatile Organic Compound Analysis, Ramesh P. Arasaradnam, Michael J. McFarlane, Courtenay Ryan-Fisher, Erik Westenbrink, Paula Hodges, Matthew G. Thomas, Samantha Chambers, Nicola O'Connell, Catherine Bailey, Christopher Harmston, Chuka U. Nwokolo, Karna D. Bardhan, James A. Covington, Plos One, 2014. Issue 9|e108750

Towards the non-invasive detection of colorectal cancer: The role of electronic noses (E-nose) and Field Asymmetric Ion Mobility Spectroscopy (FAIMS), Westenbrink E, Arasaradnam R P, O'Connell N, Bayley C, Nwokolo C, Harmston C, Bardhan K D, Covington J.

A novel tool for non invasive diagnosis and tracking of patients with Inflammatory Bowel Disease (IBD), Arasaradnam R P (MD, PhD), Ouaret N (MSc), Thomas M G (MSc), Quraishi N (MD), Heatherington E (RN), Nwokolo C U (MD, DM), Bardhan K D (MD, PhD), Covington J A (MSc, PhD).

Application of a Novel Tool for Diagnosing Bile Acid Diarrhoea, James A. Covington, Eric W. Westenbrink, Nathalie Ouaret, Ruth Harbord, Catherine Bailey, Nicola O'Connell, James Cullis, Nigel Williams, Chuka U. Nwokolo, Karna D. Bardhan, Ramesh P. Arasaradnam, Sensors, 2013. 13(9), 11899-11912

Differentiating Coeliac Disease from Irritable Bowel Syndrome by Urinary Volatile Organic Compound Analysis—A Pilot Study, Ramesh P. Arasaradnam, Eric Westenbrink, Michael J. McFarlane, Ruth Harbord, Samantha Chambers, Nicola O'Connell, Catherine Bailey, Chuka U. Nwokolo, Karna D. Bardhan, Richard Savage, James A. Covington, Plos One, 2014. Issue 10|e107312

Review article: next generation diagnostic modalities in gastroenterology—gas phase volatile compound biomarker detection, R. P. Arasaradnam, J. A. Covington, C. Harmston, C. U. Nwokolo, Wiley Online Library, 2014. Issue 8

The Detection of Patients at Risk of Gastrointestinal Toxicity during Pelvic Radiotherapy by Electronic Nose and FAIMS: A Pilot Study, James A. Covington, Linda Wedlake, Jervoise Andreyev, Nathalie Ouaret, Matthew G. Thomas, Chuka U. Nwokolo, Karna D. Bardhan, Ramesh P. Arasaradnam, Sensors, 2012. 12, 13002-13018

Towards the detection of bile acid diarrhoea: A novel non-invasive approach using electronic noses (E-nose) and Field Asymmetric Ion Mobility Spectroscopy (FAIMS), Westenbrink E, Arasaradnam R P, Thomas M, O'Connell N, Bayley C, Nwokolo C, Bardhan K D, Covington J.

LESA FAIMS mass spectrometry for the spatial profiling of proteins from tissue, Rian L. Griffiths, Andrew J. Creese, Alan Mark Race, Josephine Bunch, and Helen Jill Cooper, Anal. Chem., Just Accepted Manuscript, 2016

Determination of a Urinary Drug Metabolite using Liquid Chromatography Combined with FAIMS-MS and FAIMS-In Source CID-MS, Robert W. Smith, Danielle E. Toutoungi, James C. Reynolds, Ashley Sage, Anthony W. T. Bristow, Andrew Ray, Daniel J. Weston, Ian Wilson, Billy Boyle, Cohn S. Creaser.

Enhanced performance in the determination of ibuprofen 1-β-O-acyl glucuronide in urine by combining high field asymmetric waveform ion mobility spectrometry with liquid chromatography-time-of-flight mass spectrometry, Robert W. Smith, Danielle E. Toutoungi, James C. Reynolds, Anthony W. T. Bristow, Andrew Ray, Ashley Sage, Ian D. Wilson, Daniel J. Weston, Billy Boyle, Colin S. Creaser.

Rapid, Accurate and on-site detection of C. difficile in Stool Samples, Marije K. Bomers, Frederik P. Menke, Richard S. Savage, Christina M. J. E. Vandenbroucke-Grauls, Michiel A. van Agtmael, James A. Covington, Yvo M. Smulders. Am J Gastroenterol 2015; 110:588-594; doi: 10.1038/ajg.2015.90

Liquid extraction surface analysis field asymmetric waveform ion mobility spectrometry mass spectrometry for the analysis of dried blood spots Joscelyn Sarsby, Rian L. Griffiths, Alan Mark Race, Josephine Bunch, Elizabeth C. Randall, Andrew J. Creese, and Helen Jill Cooper, Analytical Chemistry 2015

Supervised Machine Learning and Field Asymmetric Ion Mobility Spectrometry Brian Azizi & Georgios Pilikos, University of Cambridge Non-invasive exhaled volatile organic biomarker analysis to detect inflammatory bowel disease (IBD), Ramesh P. Arasaradnam, Michael McFarlane, Emma Daulton, Jim Skinner, Nicola O'Connell, Subiatu Wurie, Samantha Chambers, Chuka Nwokolo, Karna Bardhan, Richard Savage, James Covington. Digestive and Liver Disease, 2015.

Liquid Extraction Surface Analysis Mass Spectrometry Coupled with Field Asymmetric Waveform Ion Mobility Spectrometry for Analysis of Intact Proteins from Biological Substrates, Joscelyn Sarsby, Rian L. Griffiths, Alan M. Race, Josephine Bunch, Elizabeth C. Randall, Andrew J. Creese, and Helen J. Cooper. Analytical Chemistry 2015.

Breathomics—exhaled volatile organic compound analysis to detect hepatic encephalopathy: a pilot study, R P Arasaradnam, M McFarlane, K Ling, S Wurie, N O'Connell, C U Nwokolo, K D Bardhan, J Skinner, R S Savage and J A Covington. Journal of Breath Research, 2016.

Variation in Gas and Volatile Compound Emissions from Human Urine as It Ages, Measured by an Electronic Nose, S. Esfahani, N. M. Sagar, I. Kyrou, E. Mozdiak, N. O'Connell, C. Nwokolo, K. D. Bardhan, R. P. Arasaradnam and J. A. Covington, Biosensors, 6(1), 4, 2016

The invention claimed is:

1. A wearable device for wearing on the wrist of one or more users and providing product recommendations to benefit the health of the one or more users, the device comprising:
   a wristband or wriststrap;
   a memory storing a database of product codes and associated product recommendations to benefit the health of the one or more users derived from personalised genetic information obtained from an analysis of a biological sample provided by the one or more users;
   a barcode reader reading a product code from a barcode on a product whilst the device is worn on the wrist of the one or more users;
   one or more processors, wherein one of said one or more processors uses the read product code to perform a look-up in the database to obtain a product recommendation for the associated product; and
   an indicator providing an indication of the obtained product recommendation to a wearer of the device.

2. A wearable device according to claim 1, wherein said barcode reader comprises a camera.

3. A wearable device according to claim 2, wherein said barcode reader comprises one of said one or more processors detecting the barcode within image data captured by the camera.

4. A wearable device according to claim 1 and comprising an interface for facilitating data communication with a smartphone.

5. A wearable device according to claim 4 wherein one of said one or more processors comprises a processor receiving database updates from a smartphone via said interface and for using these updates to update said database.

6. A wearable device according to claim 1 and comprising one or more physiological and/or biometric sensors and/or biosensors monitoring a wearer's genetic information, and wherein one of said one or more processors comprises a processor dynamically updating product recommendations in the database using sensed data.

7. A wearable device according to claim 1, wherein said indicator comprises a light projector projecting said indication onto a product whose product code is being read.

8. A wearable device according to claim 1 and comprising one or more motion sensors and wherein one of said one or more processors comprises a processor configured to receive data from the motion sensor(s) and determine a motion of the wearable device indicative of an intention to purchase the product.

9. A wearable device according to claim 1, wherein said personalised genetic information relates to two or more users.

10. A system comprising:
   a wearable device for wearing on the wrist of a user and providing product recommendations to benefit the health of the user, the device comprising:
   a wristband or wriststrap;
   a memory storing a database of product codes and associated product recommendations to benefit the health of the user derived from personalised genetic information obtained from an analysis of a biological sample provided by the user;
   a barcode reader reading a product code from a barcode on a product whilst the device is worn on the wrist of the user;
   a processor using the read product code to perform a look-up in the database to obtain a product recommendation for the associated product; and
   an indicator providing an indication of the obtained product recommendation to a wearer of the device; and
   a portable computer device, the portable computer device comprising a processor and memory obtaining and storing personalised genetic information of the user, using said personalised genetic information to derive product recommendations for respective products and associating the product recommendations with product codes for the products, and transmitting the product recommendations and associated product codes to the wearable device.

11. A method of providing product advice to a user to benefit the health of the user, the method comprising:
reading a product code from a barcode on a product label using a wearable computer device comprising a wristband or wriststrap worn on the wrist of the user;
interpreting the product code using genetic data stored on the device, the genetic data relating to the user and having been previously derived by means of an analysis of a biological sample obtained from the user; and
based on the interpretation, presenting on a display of the device, or indicating via some other visual, audio, or tactile interface of the device, advice relating to the product, the advice being tailored to the user.

12. A method of providing a product recommendation to a user to benefit the health of the user, the method comprising:
analysing a biological sample provided by the user in order to determine a genotype of the user;
using said genotype to determine product recommendations for consumable products;
storing in a memory of a wearable computer device, comprising a wristband or wriststrap worn on the wrist of the user, a database comprising product codes for consumable product and associated determined product recommendations;
reading a product code from a barcode on a product label using said wearable computer device;
using said read product code to perform a look-up in said database to obtain the product recommendation for the consumable product; and
presenting on a display of the device, or indicating via some other visual, audio, or tactile interface of the device, an indication of the product recommendation associated with the consumable product.

\* \* \* \* \*

SEQUENCE LISTING

```
<160> NUMBER OF SEQ ID NOS: 1

<210> SEQ ID NO 1
<211> LENGTH: 51
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (26)..(26)
<223> OTHER INFORMATION: N is A or C

<400> SEQUENCE: 1
atctctgtct cttaattatc tcacanagcc aggtattttt tattgttagc t          51
```